US012617787B2

(12) United States Patent
Lopchuk et al.

(10) Patent No.: US 12,617,787 B2
(45) Date of Patent: May 5, 2026

(54) MERGED SCAFFOLD TAF1 INHIBITORS

(71) Applicant: H. LEE MOFFITT CANCER CENTER AND RESEARCH INSTITUTE, INC., Tampa, FL (US)

(72) Inventors: Justin M. Lopchuk, Tampa, FL (US); Ernst Schonbrunn, Tampa, FL (US); Zachary Shultz, Lakeland, FL (US); Md Rezaul Karim, Belmont, CA (US); Jiandong Chen, Tampa, FL (US)

(73) Assignee: LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 525 days.

(21) Appl. No.: 18/039,386

(22) PCT Filed: Nov. 30, 2021

(86) PCT No.: PCT/US2021/061121

§ 371 (c)(1),
(2) Date: May 30, 2023

(87) PCT Pub. No.: WO2022/115753

PCT Pub. Date: Jun. 2, 2022

(65) Prior Publication Data

US 2024/0002378 A1 Jan. 4, 2024

Related U.S. Application Data

(60) Provisional application No. 63/119,287, filed on Nov. 30, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ............................ C07D 471/04; C07D 519/00
See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |
| 5,167,649 | A | 12/1992 | Zook |
| 6,960,648 | B2 | 11/2005 | Bonny |
| 2002/0035243 | A1 | 3/2002 | Imfeld et al. |
| 2002/0120100 | A1 | 8/2002 | Bonny |
| 2003/0032594 | A1 | 2/2003 | Bonny |
| 2011/0306613 | A1 * | 12/2011 | Foote ...................... A61P 43/00 544/122 |
| 2017/0340605 | A1 * | 11/2017 | Albrecht ................. A61P 37/02 |
| 2019/0023689 | A1 | 1/2019 | Song et al. |
| 2019/0117641 | A1 | 4/2019 | Sdelci et al. |
| 2024/0150333 | A1 * | 5/2024 | Schonbrunn ......... C07D 413/04 |
| 2024/0398800 | A1 * | 12/2024 | Lopchuk .............. A61K 31/506 |

OTHER PUBLICATIONS

Wang; J. Med. Chem. 2018, 61, 20, 9301-9315. https://doi.org/10.1021/acs.jmedchem.8b01225 (Year: 2018).*
International search report and written opinion in PCT/US2021/061121. Mailed Mar. 21, 2022. 12 pages.
Foote et al., Discovery and Characterization of AZD6738, a Potent Inhibitor of Ataxia Telangiectasia Mutated and Rad3 Related (ATR) Kinase with Application as an Anticancer Agent, Journal of Medicinal Chemistry, vol. 61, Oct. 22, 2018.
Karim et al, Crystal structure of the tandem bromodomain of human TAF1 (TAF1-T) pound to ZS1-681, WorldWide Protein Data Bank, Jun. 3, 2021.
Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17.

* cited by examiner

*Primary Examiner* — Daniel R Carcanague
(74) *Attorney, Agent, or Firm* — Meunier Carlin & Curfman LLC

(57) ABSTRACT

Disclosed are inhibitors for TAF1. Methods of using the disclosed compounds to treat cancer are also disclosed.

20 Claims, 7 Drawing Sheets

*Synthesis of GNE371 Fragment:*

*Synthesis of AZD6738 Fragment:*

*Convergent Coupling of Both Fragments:*

MERGED SCAFFOLD TAF1 INHIBITORS

CROSS-REFERENCE TO RELATED APPLICATIONS

This application is a United States National Phase Patent Application of International Patent Application No. PCT/US2021/061121, filed Nov. 30, 2021, which claims the benefit of priority to U.S. Provisional Application No. 63/119,287, filed Nov. 30, 2020, the disclosure of which is incorporated herein by reference in its entirety.

BACKGROUND

Bromodomains (BRD) are highly conserved epigenetic "reader" modules that specifically recognize N-acetylated lysine (KAc) residues on histones and other proteins. Bromodomain-containing proteins control numerous functions including gene transcription and chromatin remodeling, gene splicing, protein scaffolding and signal transduction, and therefore, play fundamental roles in cell proliferation and division. A number of BRD-containing proteins, particularly those of the bromodomain and extra-terminal (BET) family, have been linked to tumorigenesis and inflammatory diseases. The landmark discoveries of potent small molecule inhibitors of BET bromodomains provided chemical tools to explore the function of proteins such as BRD4 in disease states for the first time. Since then several BRD4 inhibitors have entered clinical trials for oncology and cardiovascular indications. More recently, inhibitors targeting non-BET bromodomains, for which the physiological functions are not yet well understood, have been the subject of intense efforts in academia and pharmaceutical industry alike. Such inhibitors are valuable probes to unravel the function of bromodomains outside the BET family, their relevance in cancer and their potential as drug targets.

The bromodomain-containing protein TAF1 (TATA-box binding protein associated factor 1) is a subunit of the core promoter recognizing complex TFIID involved in general transcription. It is composed of several domains, a TBP (TATA binding protein) binding domain, an N-terminal kinase domain, a domain of unidentified function (DUF3591), a histone acetyltransferase domain, a winged-helix domain, a zinc knuckle motif, a tandem bromodomain (BD1 and BD2), a serine rich acidic tail domain, and a C-terminal kinase domain (FIG. 1). Recently, genomic landscape studies identified TAF1 as a significantly mutated gene in uterine serous carcinoma, and TAF1 overexpression has been described as a major factor for the high mitotic activity of human lung and breast carcinoma cells. TAF1 has been reported to inactivate p53 through phosphorylation at Thr55, translocating p53 to the cytoplasm and Mdm2-mediated degradation to induce G1/S-transition.24-26 Upon DNA damage, diacetylated p53 (K373ac and K382ac) directly interacts with the bromodomains of TAF1 to initiate gene transcription. Inactivation of TAF1 has been associated with activation of DNA damage response, similar to that mediated by ATR (Ataxia telangiectasia and Rad3-related protein). Temperature-sensitive mutations in the putative HAT domain of TAF1 caused p53 activation and cell cycle arrest, hallmarks of an ATR-mediated DNA damage response.

Although deregulation of gene transcription and evolving plasticity are the underlying cause of ever increasing drug resistance in cancer, TAF1 remains an underexplored target for the development of drugs aimed at uncontrolled gene transcription. Recent advancements in chemical biology and drug development indicate that targeting the basal transcription machinery is a viable means to develop promising new drugs. However, none of these approaches addressed the targeted inhibition of TAF1. To date, only few bromodomain inhibitors of TAF1 have been reported, with compounds BAY299 and GNE-371 being the most potent. Activity of these two compounds against the cancer cell lines tested was weak or not reported, but antiproliferative synergy with the BET inhibitor JQ1 was demonstrated. No TAF1 inhibitor has reached the clinic, and biological effects of inhibiting the bromodomain of TAF1 have not been reported yet.

Combined, the present knowledge suggests that TAF1 is a promising yet underexplored target for the development of small molecule inhibitors directed at the transcription machinery of cancer cells through an epigenetic mechanism of action. There is a need for compositions and methods for chemical inhibition of the bromodomain of TAF1 alone and in combination with ATR in cancer. The precise role of the tandem bromodomain of TAF1 in the upregulation of oncogenic or inactivation of apoptotic pathways is unclear, and the effect of chemical TAF1 inhibition on transcriptional activity has not been reported yet. Previously, it was shown that TAF1 regulates cyclin A and D1 gene expression, Rb phosphorylation, DNA damage response (DDR) pathways and p21/p27 expression. However, the contribution of bromodomains in these signaling pathways is not known. Inhibiting the DDR has become a therapeutic concept in cancer therapy. Resistance to genotoxic therapies has been associated with increased DDR signaling, and many cancers are dependent on the functional DDR pathways for survival What are needed are new, potent and selective inhibitors for TAF1 and methods for their use. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions. The compounds can have a structure represented by Formula I.

Formula I

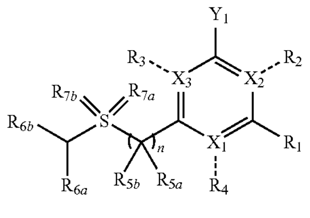

wherein $X_1$, $X_2$, and $X_3$ are independently selected from C, N, or S;

$Y_1$ is selected from a GNE-371 (a selective chemical probe for the second bromodomains of human transcription-initiation-factor TFIID subunit 1 and transcription-initiation-factor TFIID subunit 1-like) fragment; an aryl, a heteroaryl, a cycloalkenyl, a cycloheteroalkenyl, wherein $Y_1$ is substituted or substituted;

$R_1$ is substituted or unsubstituted aryl and heteroaryl;

$R_2$, $R_3$, and $R_4$, when present, are independently selected from, hydrogen, halogen, hydroxyl, cyano, carboxyl, $C_1$-$C_3$ alkyl, $C_1$-$C_3$ haloalkyl, or cyclopropyl;

$R_{5a}$ and $R_{5b}$, independent for each occurrence, are independently selected from, hydrogen, halogen, hydroxyl, cyano, carboxyl, amino, substituted or unsubstituted aminoalkyl, substituted or unsubstituted $C_1$-$C_6$ alkyl, substituted or unsubstituted $C_1$-$C_6$ haloalkyl, substituted or unsubstituted cycloalkyl, substituted or unsubstituted cycloheteroalkyl, or $R_{5a}$ and $R_{5b}$ combine together with the atom to which they are attached to form a $C_3$-$C_8$ cycloalkyl or a $C_2$-$C_7$ heterocycloalkyl;

$R_{6a}$ and $R_{6b}$ are independently selected from, hydrogen, halogen, hydroxyl, cyano, carboxyl, amino, substituted or unsubstituted aminoalkyl, substituted or unsubstituted $C_1$-$C_6$ alkyl, substituted or unsubstituted $C_1$-$C_6$ haloalkyl, substituted or unsubstituted cycloalkyl, substituted or unsubstituted cycloheteroalkyl, or $R_{5a}$ and $R_{5b}$ combine together with the atom to which they are attached to form a $C_3$-$C_8$ cycloalkyl or a $C_2$-$C_7$ heterocycloalkyl; or wherein two or more of $R_{5a}$, $R_{5b}$, $R_{6a}$, and $R_{6b}$ combine together with the atom to which they are attached to form a $C_2$-$C_7$ heterocycloalkyl or $C_2$-$C_7$ heterocycloalkenyl;

$R_{7a}$ and $R_{7b}$ are independently selected from O or NH;

n is an integer selected from 1-5;

----- represents a bond that is present or absent, or a pharmaceutically acceptable salt thereof.

In some embodiments, the compound of Formula I may be a compound of Formula I-A:

(I-A)

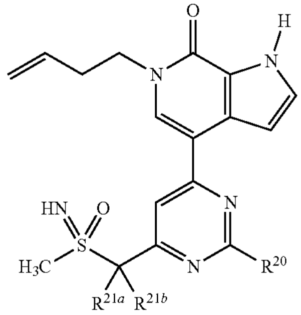

or a pharmaceutically acceptable salt thereof, wherein:

$R^{20}$ is selected from unsubstituted or substituted aryl and unsubstituted or substituted heteroaryl; and $R^{21a}$ and $R^{21b}$ are brought together with the carbon atom to which they are attached to form a cycloalkyl or a heterocycloalkyl ring.

In an alternative aspect, a compound of Formula II is provided:

(II)

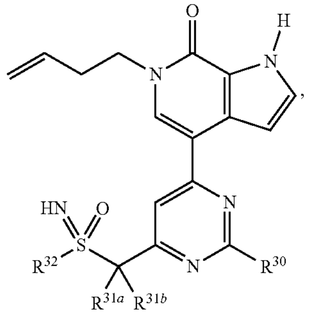

or a pharmaceutically acceptable salt thereof, wherein:

$R^{30}$ is selected from $R^{30a}$ or —NH—$R^{30a}$;

$R^{30a}$ is selected from unsubstituted or substituted aryl, unsubstituted or substituted heteroaryl, substituted or unsubstituted cycloalkyl, and unsubstituted or substituted heterocycloalkyl;

$R^{31a}$ and $R^{31b}$ are brought together with the carbon to which they are attached to form a substituted or unsubstituted cycloalkyl ring or a substituted or unsubstituted heterocycloalkyl ring;

$R^{32}$ is selected from $R^{32a}$ or —NH—$R^{32b}$;

$R^{32a}$ is selected from substituted or unsubstituted $C_1$-$C_6$ alkyl, substituted or unsubstituted aryl, substituted or unsubstituted cycloalkyl, substituted or unsubstituted heterocycloalkyl, —($C_1$-$C_6$ alkyl)-(substituted or unsubstituted aryl), —($C_1$-$C_6$ alkyl)-(substituted or unsubstituted heteroaryl), —($C_1$-$C_6$ alkyl)-(substituted or unsubstituted cycloalkyl), and —($C_1$-$C_6$ alkyl)-(substituted or unsubstituted heterocyloalkyl); and $R^{32b}$ is selected from hydrogen, substituted or unsubstituted $C_1$-$C_6$ alkyl, substituted or unsubstituted aryl, substituted or unsubstituted cycloalkyl, substituted or unsubstituted heterocycloalkyl, —($C_1$-$C_6$ alkyl)-(substituted or unsubstituted aryl), —($C_1$-$C_6$ alkyl)-(substituted or unsubstituted heteroaryl), —($C_1$-$C_6$ alkyl)-(substituted or unsubstituted cycloalkyl), and —($C_1$-$C_6$ alkyl)-(substituted or unsubstituted heterocyloalkyl).

Pharmaceutical compositions comprising a therapeutically effective amount of a compound described herein or a pharmaceutically acceptable salt thereof, and a pharmaceutically acceptable carrier are also disclosed.

In specific aspects, the disclosed subject matter relates to cancer therapy and to anti-cancer compounds. More specifically, the subject matter disclosed herein relates to inhibitors for the bromodomain-containing protein TAF1 (transcription initiation factor TFIID subunit 1). Further, the subject matter disclosed herein relates to inhibitors that are selective for TAF1. Also disclosed are methods of inhibiting the second bromodomain of TAF1. Methods of treating certain cancers are disclosed herein. In certain examples, the cancer is breast cancer or lung cancer.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DESCRIPTION OF DRAWINGS

FIG. 1A shows the preparation of the GNE371 fragment. FIG. 1B shows the preparation of the AZD6738 fragment. FIG. 1C shows the convergent coupling of both fragments.

FIG. 3A shows the ATR inhibitor AZD6738 positive control.

FIG. 3B shows the absence of inhibition by ZS1-681 and GNE371.

Like reference symbols in the various drawings indicate like elements.

DETAILED DESCRIPTION

Figure 1A:
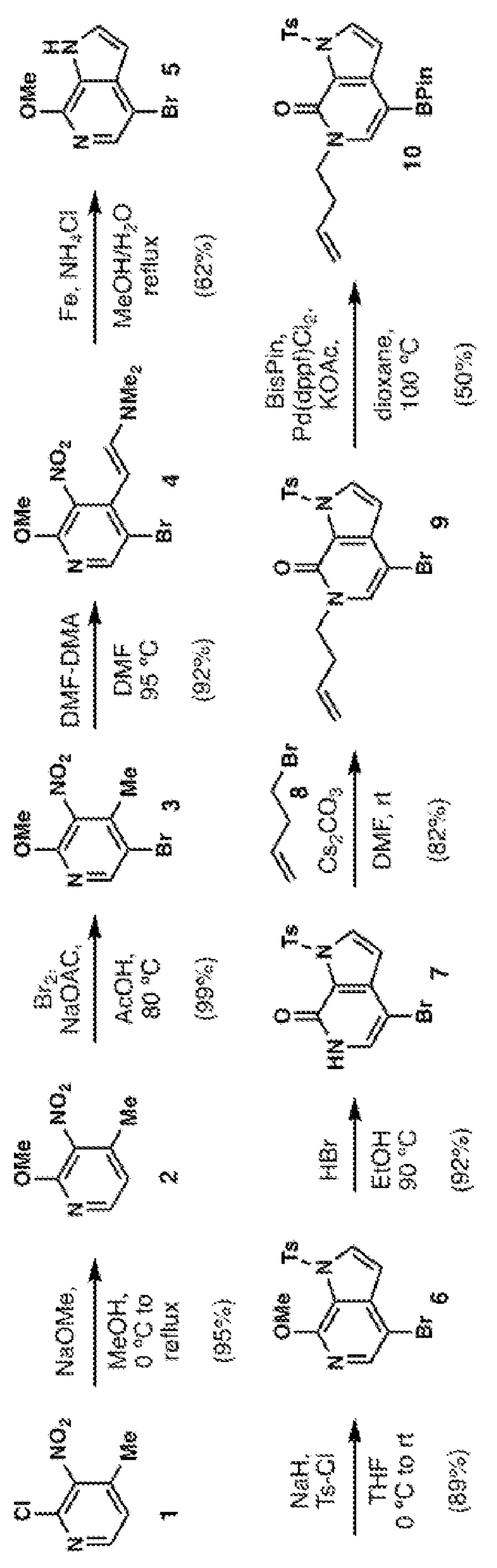
FIGS. 1A, 1B, and 1C show a reaction scheme for the preparation of representative compound ZS1-681 as described in Example 1.
Figure 1B:
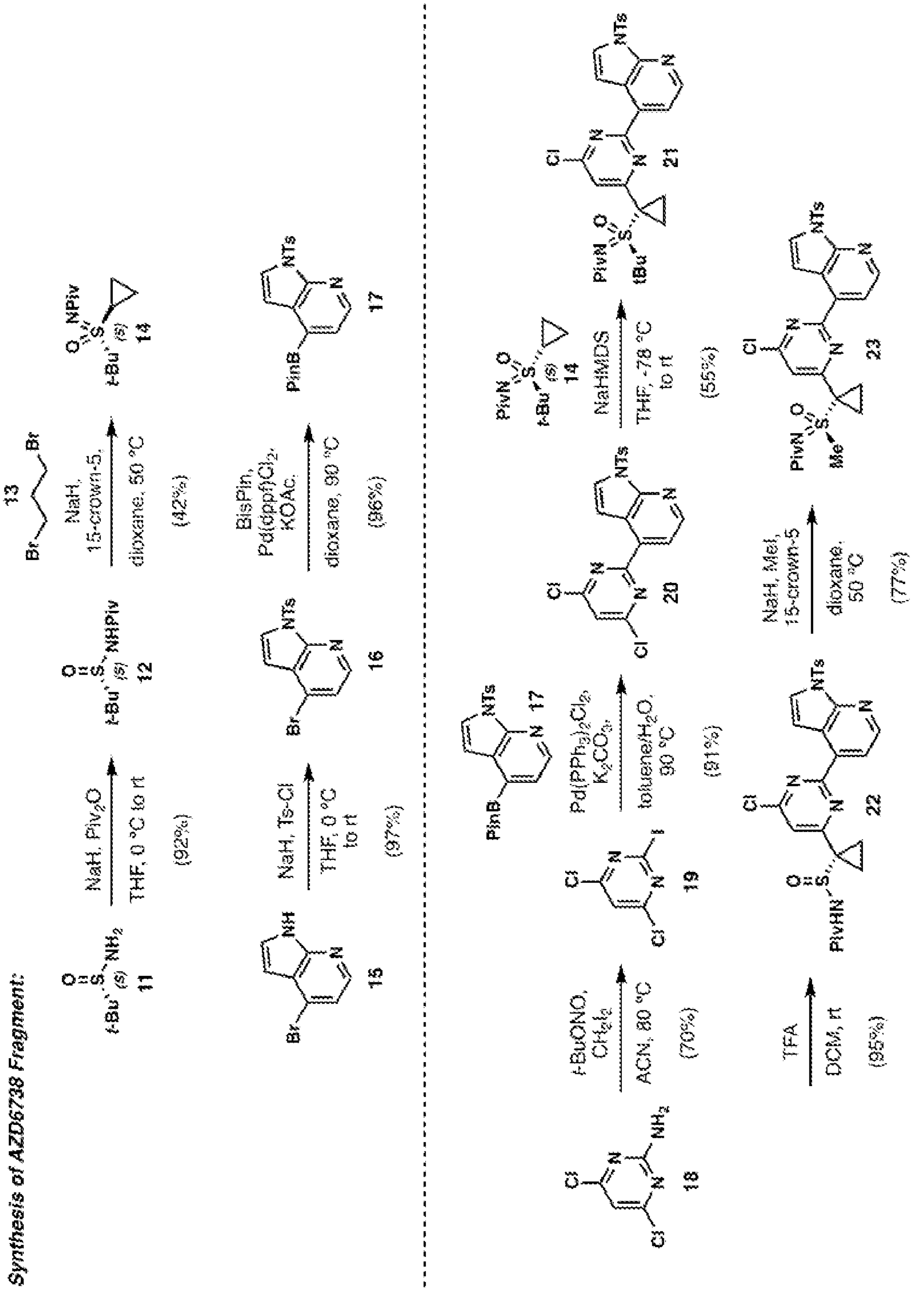
Figure 1C:
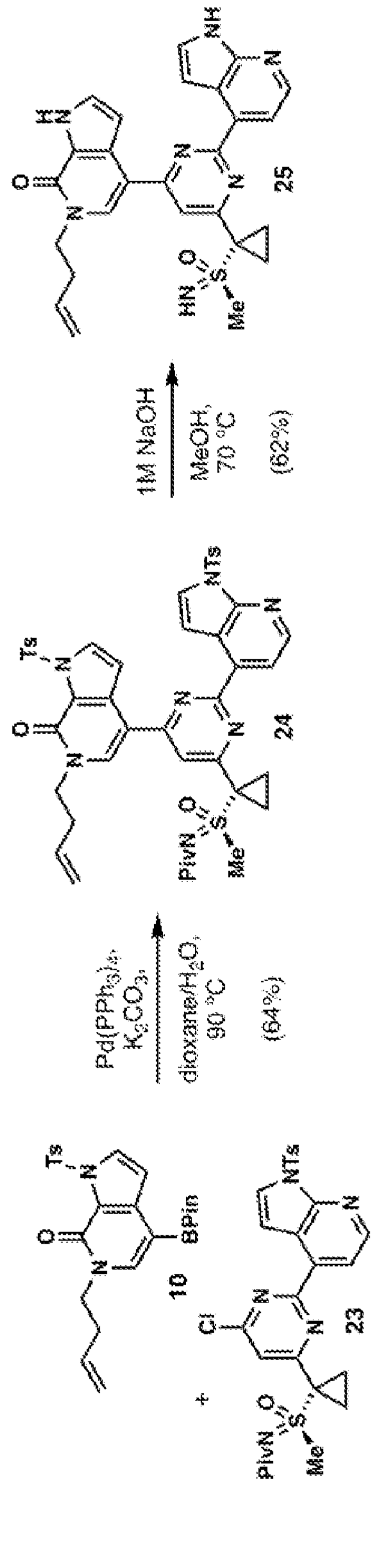
Figure 2:
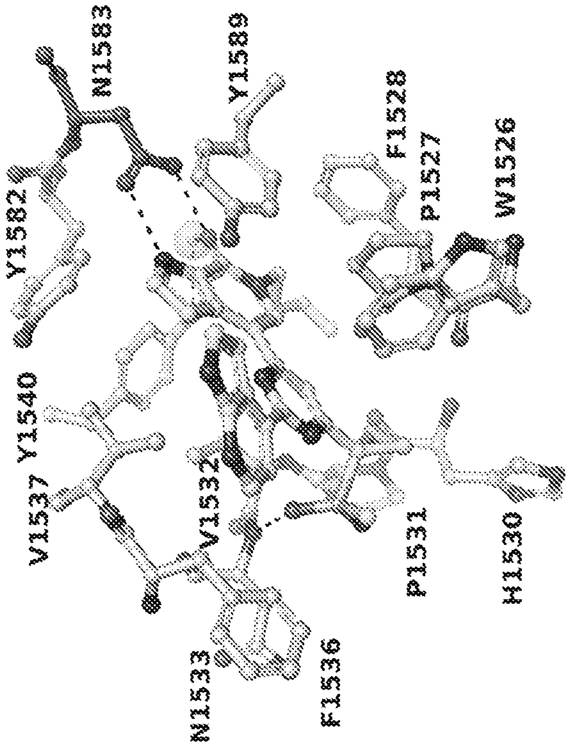
FIG. 2 shows a cocrystal structure of TAF1 liganded with merged scaffold compound ZS1-681 whose preparation is described in example 1.
Figure 3A:
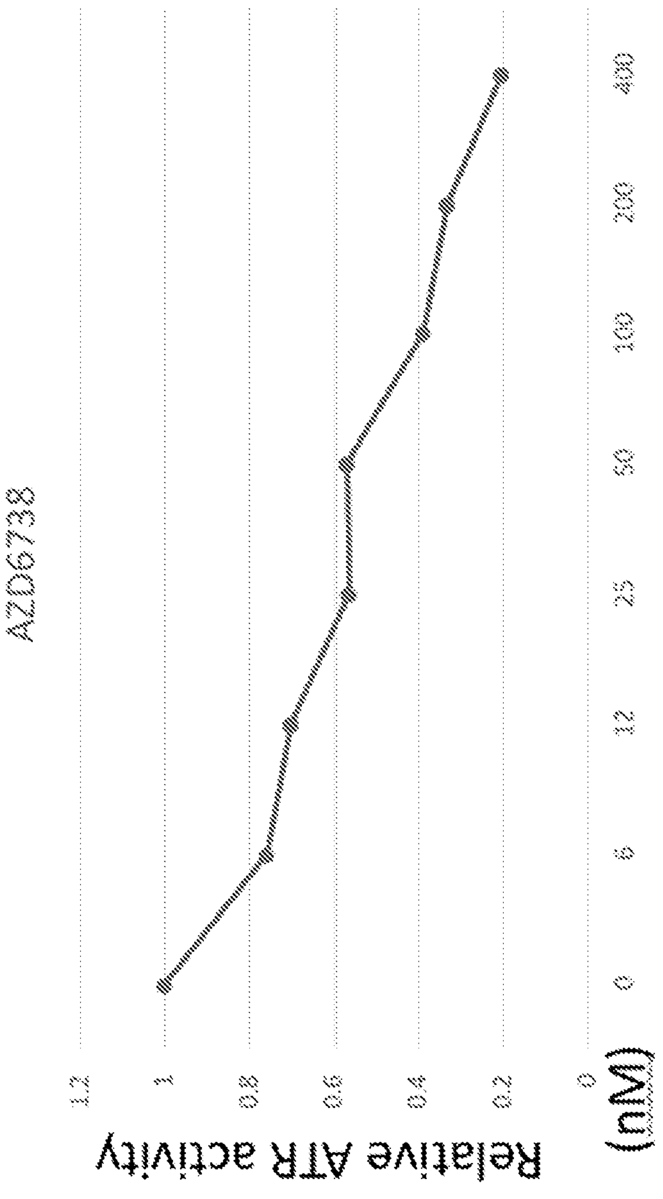
FIGS. 3A and 3B show that ZS1-681 does not inhibit ATR. ELISA-based kinase activity was used to test the ability of compounds to inhibit phosphorylation of p53 S15 by purified FLAG-ATR in vitro.
Figure 3B:
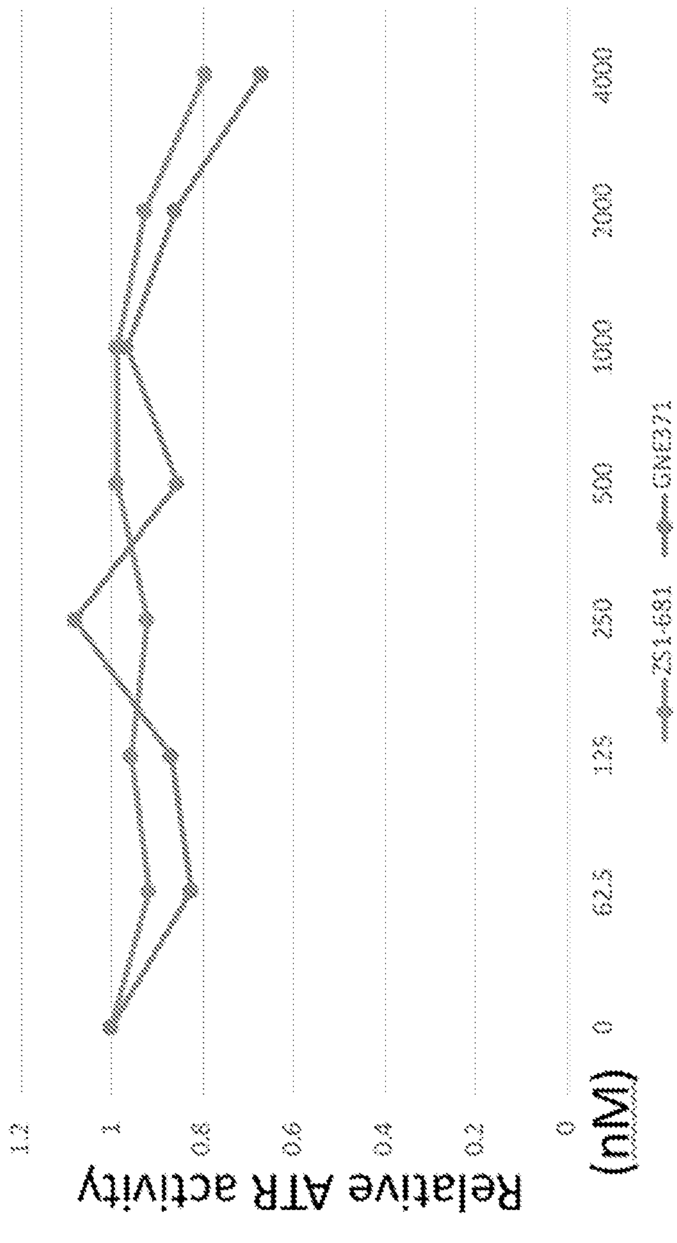
Figure 4:
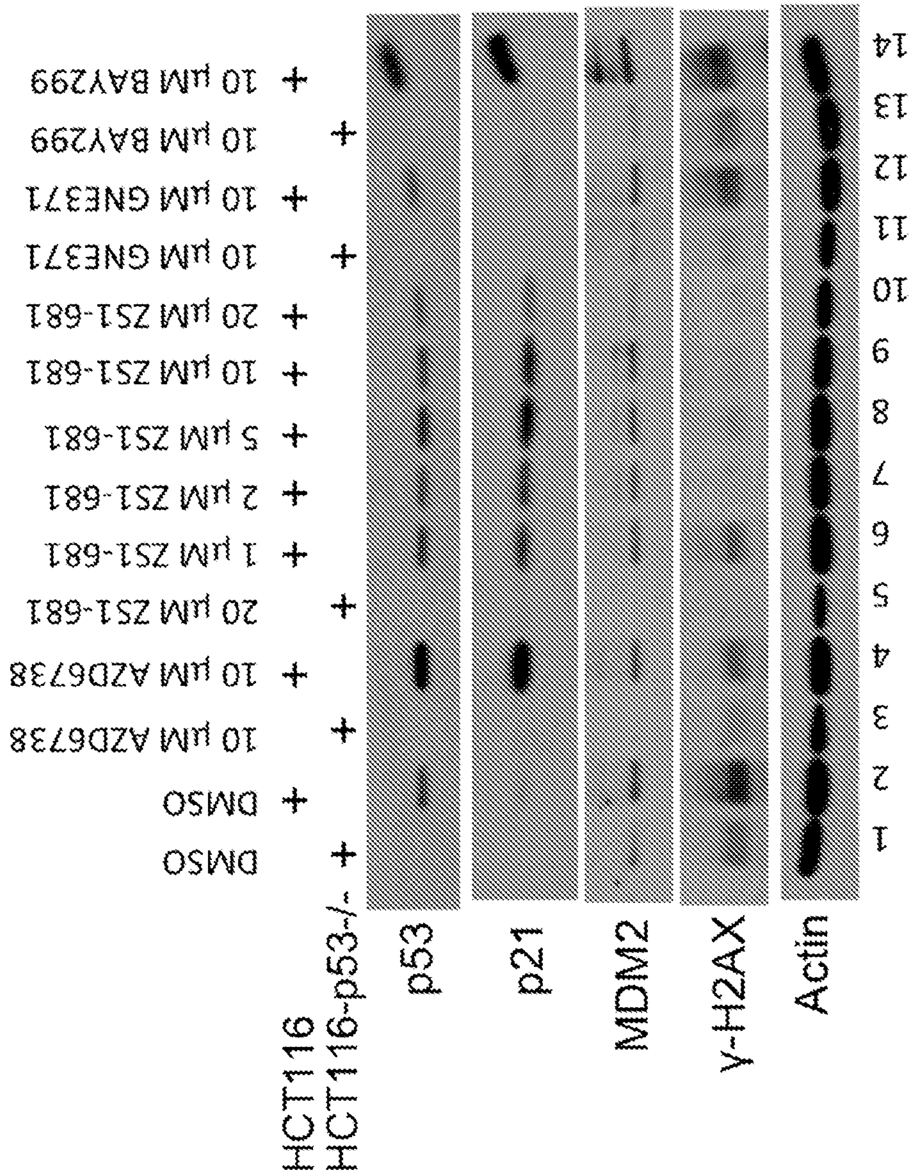
FIG. 4 shows that ZS1-681 induces p53-mediated p21 expression. HCT116 cells with and without p53 were treated with compounds for 30 hrs. Expression levels of indicated markers were determined by western blot.

The materials, compounds, compositions, and methods described herein may be understood more readily by reference to the following detailed description of specific aspects of the disclosed subject matter and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an inhibitor" includes mixtures of two or more such inhibitors, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., tumor growth, metastasis). It is understood that this is typically in relation to some standard or expected value, in other words it is relative, but that it is not always necessary for the standard or relative value to be referred to. For example, "reduces tumor growth" means decreasing the amount of tumor cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as tumor growth or metastasis), diminishment of extent of cancer, stabilized (i.e., not worsening) state of cancer, preventing or delaying spread (e.g., metastasis) of the cancer, delaying occurrence or recurrence of cancer, delay or slowing of cancer progression, amelioration of the cancer state, and remission (whether partial or total).

The term "patient" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valencies of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The symbols $A^n$ is used herein as merely a generic substituent in the definitions below.

The term "alkoxy" as used herein is an alkyl group bound through a single, terminal ether linkage; that is, an "alkoxy" group can be defined as —$OA^1$ where $A^1$ is alkyl as defined above.

The term "alkenyl" as used herein is a hydrocarbon group of from 2 to 24 carbon atoms with a structural formula containing at least one carbon-carbon double bond. Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C═O.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" as used herein is represented by the formula $—C(O)O^-$.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula $—NO_2$.

The term "cyano" as used herein is represented by the formula —CN

The term "azido" as used herein is represented by the formula $—N_3$.

The term "sulfonyl" is used herein to refer to the sulfo-oxo group represented by the formula $—S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula $—S(O)_2NH_2$.

The term "thiol" as used herein is represented by the formula —SH.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

In certain aspects, disclosed herein are compounds having Formula I:

Formula I

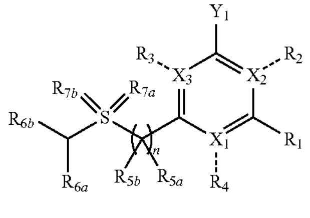

wherein $X_1$, $X_2$, and $X_3$ are independently selected from C, N, or S;

$Y_1$ is selected from a GNE-371 (a selective chemical probe for the second bromodomains of human transcription-initiation-factor TFIID subunit 1 and transcription-initiation-factor TFIID subunit 1-like) fragment; an aryl, a heteroaryl, a cycloalkenyl, a cycloheteroalkenyl, wherein $Y_1$ is substituted or substituted;

$R_1$ is substituted or unsubstituted aryl and heteroaryl;

$R_2$, $R_3$, and $R_4$, when present, are independently selected from, hydrogen, halogen, hydroxyl, cyano, carboxyl, $C_1$-$C_3$ alkyl, $C_1$-$C_3$ haloalkyl, or cyclopropyl;

$R_{5a}$ and $R_{5b}$, independent for each occurrence, are independently selected from, hydrogen, halogen, hydroxyl, cyano, carboxyl, amino, substituted or unsubstituted aminoalkyl, substituted or unsubstituted $C_1$-$C_6$ alkyl, substituted or unsubstituted $C_1$-$C_6$ haloalkyl, substituted or unsubstituted cycloalkyl, substituted or unsubstituted cycloheteroalkyl, or $R_{5a}$ and $R_{5b}$ combine together with the atom to which they are attached to form a $C_3$-$C_8$ cycloalkyl or a $C_2$-$C_7$ heterocycloalkyl;

$R_{6a}$ and $R_{6b}$ are independently selected from, hydrogen, halogen, hydroxyl, cyano, carboxyl, amino, substituted or unsubstituted aminoalkyl, substituted or unsubstituted $C_1$-$C_6$ alkyl, substituted or unsubstituted $C_1$-$C_6$ haloalkyl, substituted or unsubstituted cycloalkyl, substituted or unsubstituted cycloheteroalkyl, or $R_{5a}$ and $R_{5b}$ combine together with the atom to which they are attached to form a $C_3$-$C_8$ cycloalkyl or a $C_2$-$C_7$ heterocycloalkyl; or wherein two or more of $R_{5a}$, $R_{5b}$, $R_{6a}$, and $R_{6b}$ combine together with the atom to which they are attached to form a $C_2$-$C_7$ heterocycloalkyl or $C_2$-$C_7$ heterocycloalkenyl;

$R_{7a}$ and $R_{7b}$ are independently selected from O or NH;

n is an integer selected from 1-5;

----- represents a bond that is present or absent, or a pharmaceutically acceptable salt thereof.

Also disclosed are pharmaceutical compositions comprising a therapeutically effective amount of a disclosed compound, or a pharmaceutically acceptable salt thereof, and a pharmaceutically acceptable carrier.

In some aspects of Formula I, $R^1$ can include a substituted aryl or a substituted or unsubstituted heteroaryl. For example, $R^1$ can include a 5-, 6- and 7-membered aromatic ring. The ring can be a carbocyclic, heterocyclic, fused carbocyclic, fused heterocyclic, bicarbocyclic, or biheterocyclic ring system, which is optionally substituted as described herein. In some embodiments when $R^1$ is an heteroaryl, $R^1$ can include a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_5$) alkyl, phenyl or benzyl. Examples of aryl and heteroaryl rings include, but are not limited to, benzene, pyrrole, furan, thiophene, imidazole, oxazole, thiazole, triazole, pyrazole, pyridine, pyrazine, pyridazine and pyrimidine. The aromatic ring can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN.

In some embodiments, $R^1$ includes a polycyclic aryl or heteroaryl ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic. For example, in some embodiments when $R^1$ is a heteroaryl, $R^1$ can include an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

In specific examples, $R^1$ is selected from a substituted $C_5$-$C_6$ aryl or a substituted or unsubstituted $C_2$-$C_9$ heteroaryl. For example, $R^1$ can be selected from a substituted phenyl, substituted or unsubstituted furyl, substituted or unsubstituted imidazolyl, substituted or unsubstituted triazolyl, substituted or unsubstituted triazinyl, substituted or unsubstituted oxazoyl, substituted or unsubstituted isoxazoyl, substituted or unsubstituted thiazolyl, substituted or unsubstituted isothiazoyl, substituted or unsubstituted pyrazolyl, substituted or unsubstituted pyrrolyl, substituted or unsubstituted pyrazinyl, substituted or unsubstituted tetrazolyl, substituted or unsubstituted pyridyl, substituted or unsubstituted thienyl, substituted or unsubstituted pyrimidinyl, substituted or unsubstituted indolyl, substituted or unsubstituted isoquinolyl, substituted or unsubstituted quinolyl, substituted or unsubstituted benzothienyl, substituted or unsubstituted benzofuranyl, substituted or unsubstituted benzoxazolyl, substituted or unsubstituted benzimidazolyl, substituted or unsubstituted benzothiazolyl, substituted or unsubstituted isoindolyl, substituted or unsubstituted indolinyl, substituted or unsubstituted isoindolinyl, substituted or unsubstituted substituted or unsubstituted quinoxalinyl, substituted or unsubstituted quinazolinyl, substituted or unsubstituted cinnolinyl, substituted or unsubstituted [2,3-c] or [3,2-c]-thienopyridyl, and the like. In some examples, $R^1$ is a substituted or unsubstituted fused $C_4$-$C_9$ heteroaryl, preferably unsubstituted indolyl.

In some aspects of Formula I, $X_1$ is selected from C or N. In some embodiments, $X_1$ is C. In other embodiments, $X_1$ is or N.

In some aspects of Formula I, $X_2$ is selected from C or N. In some embodiments, $X_2$ is C. In other embodiments, $X_2$ is or N.

In some aspects of Formula I, $X_3$ is selected from C or N. In some embodiments, $X_3$ is C. In other embodiments, $X_3$ is or N.

In some aspects of Formula I, $X_1$, $X_2$, and $X_3$ are the same or different. In some embodiments, $X_1$ and $X_2$ are both N. In some embodiments, $X_1$ and $X_3$ are both N. In some embodiments, $X_2$ and $X_3$ are both N. In some embodiments, $X_1$, $X_2$, and $X_3$ are all N. In some embodiments, $X_1$, $X_2$, and $X_3$ are all C.

In some aspects of Formula I, $Y_1$ is selected from a GNE-371 fragment or a substituted cycloheteroalkenyl (preferably a substituted bicycloheteroalkenyl). In some embodiments, wherein $Y_1$ is substituted with a moiety that promotes hydrogen bonding.

In some aspects of Formula I, $R_2$, $R_3$, and $R_4$, when present, are independently selected from, hydrogen, halogen, hydroxyl, cyano, carboxyl, $C_1$-$C_3$ alkyl, $C_1$-$C_3$ haloalkyl, or cyclopropyl. When $X_1$ and $X_2$ are both N and $R_2$ and $R_4$ may be absent. In some examples, $X_3$ can be C and $R_3$ is present and selected from hydrogen or $C_1$-$C_3$ alkyl.

In some aspects of Formula I, $R_{5a}$ and $R_{5b}$, independent for each occurrence, are independently selected from, hydrogen, amino, substituted or unsubstituted aminoalkyl, substituted or unsubstituted $C_1$-$C_6$ alkyl, substituted or unsubstituted $C_1$-$C_6$ haloalkyl, substituted or unsubstituted cycloalkyl, substituted or unsubstituted cycloheteroalkyl, or $R_{5a}$ and $R_{5b}$ combine together with the atom to which they are attached to form a $C_3$-$C_5$ cycloalkyl or a $C_2$-$C_4$ heterocycloalkyl. For example, $R_{5a}$ and $R_{5b}$, independent for each occurrence, can be independently selected from, hydrogen, substituted or unsubstituted $C_1$-$C_6$ alkyl, or substituted or unsubstituted $C_1$-$C_6$ haloalkyl, substituted or unsubstituted cycloalkyl.

In some aspects of Formula I, $R_{6a}$ and $R_{6b}$ are independently selected from, hydrogen, amino, substituted or unsubstituted aminoalkyl, substituted or unsubstituted $C_1$-$C_6$ alkyl, substituted or unsubstituted $C_1$-$C_6$ haloalkyl, substituted or unsubstituted cycloalkyl, substituted or unsubstituted cycloheteroalkyl, or $R_{6a}$ and $R_{6b}$ combine together with the atom to which they are attached to form a $C_3$-$C_8$ cycloalkyl or a $C_2$-$C_4$ heterocycloalkyl. For example, $R_{6a}$ and $R_{6b}$ can be independently selected from, hydrogen, substituted or unsubstituted $C_1$-$C_6$ alkyl, or substituted or unsubstituted $C_1$-$C_6$ haloalkyl, substituted or unsubstituted cycloalkyl.

In some embodiments, the compound of Formula I may be a compound of Formula I-A:

(I-A)

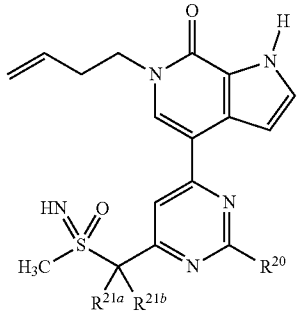

or a pharmaceutically acceptable salt thereof, wherein:

$R^{20}$ is selected from unsubstituted or substituted aryl and unsubstituted or substituted heteroaryl; and $R^{21a}$ and $R^{21b}$ are brought together with the carbon atom to which they are attached to form a cycloalkyl or a heterocycloalkyl ring.

In some embodiments of Formula I-A, $R^{20}$ can include a substituted aryl or a substituted or unsubstituted heteroaryl. For example, $R^{20}$ can include a 5-, 6- and 7-membered aromatic ring. The ring can be a carbocyclic, heterocyclic, fused carbocyclic, fused heterocyclic, bicarbocyclic, or biheterocyclic ring system, which is optionally substituted as described herein. In some embodiments when $R^{20}$ is an heteroaryl, $R^{20}$ can include a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_8$) alkyl, phenyl or benzyl. Examples of aryl and heteroaryl rings include, but are not limited to, benzene, pyrrole, furan, thiophene, imidazole, oxazole, thiazole, triazole, pyrazole, pyridine, pyrazine, pyridazine and pyrimidine. The aromatic ring can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN.

In some embodiments of Formula I-A, $R^{20}$ includes a polycyclic aryl or heteroaryl ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic. For example, in some embodiments when $R^{20}$ is a heteroaryl, $R^{20}$ can include an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

In specific examples of Formula I-A, $R^{20}$ is selected from a substituted $C_5$-$C_6$ aryl or a substituted or unsubstituted $C_2$-$C_9$ heteroaryl. For example, $R^{20}$ can be selected from a substituted phenyl, substituted or unsubstituted furyl, substituted or unsubstituted imidazolyl, substituted or unsubstituted triazolyl, substituted or unsubstituted triazinyl, substituted or unsubstituted oxazoyl, substituted or unsubstituted isoxazoyl, substituted or unsubstituted thiazolyl, substituted or unsubstituted isothiazoyl, substituted or unsubstituted pyrazolyl, substituted or unsubstituted pyrrolyl, substituted or unsubstituted pyrazinyl, substituted or unsubstituted tetrazolyl, substituted or unsubstituted pyridyl, substituted or unsubstituted thienyl, substituted or unsubstituted pyrimidinyl, substituted or unsubstituted indolyl, substituted or unsubstituted isoquinolyl, substituted or unsubstituted quinolyl, substituted or unsubstituted benzothienyl, substituted or unsubstituted benzofuranyl, substituted or unsubstituted benzoxazolyl, substituted or unsubstituted benzimidazoly, substituted or unsubstituted benzothiazolyl, substituted or unsubstituted isoindolyl, substituted or unsubstituted indolinyl, substituted or unsubstituted isoindolinyl, substituted or unsubstituted substituted or unsubstituted quinoxalinyl, substituted or unsubstituted quinazolinyl, substituted or unsubstituted cinnolinyl, substituted or unsubstituted [2,3-c] or [3,2-c]-thienopyridyl, and the like. In some examples, $R^{20}$ is a substituted or unsubstituted fused $C_4$-$C_9$ heteroaryl, preferably unsubstituted indolyl.

In some embodiments of Formula I-A, $R^{20}$ is

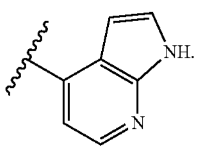 [SMILES: *c1ccnc2[nH]ccc12]

In some embodiments of Formula I-A, $R^{20}$ is

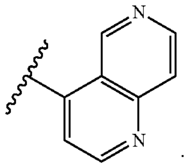 [SMILES: *c1ccnc2ccncc12]

In some embodiments of Formula I-A, $R^{20}$ is

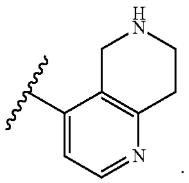 [SMILES: *c1ccnc2c1CNCC2]

In some embodiments of Formula I-A, $R^{21a}$ and $R^{21b}$ may be brought together with the carbon to which they are attached to form a cycloalkyl ring. For example, $R^{21a}$ and $R^{21b}$ may be brought together with the carbon to which they are attached to form a cyclopropyl ring, a cyclobutyl ring, a cyclopentyl ring, or a cyclohexyl ring. In particular embodiments, $R^{21a}$ and $R^{21b}$ may be brought together with the carbon to which they are attached to form a cyclopropyl ring or a cyclobutyl ring. In particular examples, $R^{21a}$ and $R^{21b}$ may be brought together with the carbon to which they are attached to form a cyclopropyl ring.

In some embodiments of Formula I-A, $R^{21a}$ and $R^{21b}$ may be brought together with the carbon to which they are attached to form a heterocycloalkyl ring containing at least one ring heteroatom (for example, 1 or 2 ring heteroatoms) selected from —O—, —N($Y^1$)—, and S, wherein $Y^1$ is hydrogen, $C_1$-$C_6$ alkyl, cycloalkyl, aryl, or heteroaryl. In particular embodiments, $R^{21a}$ and $R^{21b}$ may be brought together with the carbon to which they are attached to form a heterocycloalkyl ring containing 1 or 2 ring heteroatoms selected from —O— and —N($Y^1$)—. In particular embodiments, $R^{21a}$ and $R^{21b}$ may be brought together with the carbon atom to which they are attached to form a 3- to 6-membered heterocycloalkyl ring containing 1 or 2 ring oxygen atoms. In particular embodiments, $R^{21a}$ and $R^{21b}$ may be brought together with the carbon to which they are attached to form a 3- to 6-membered heterocycloalkyl ring containing 1 or 2 ring nitrogen atoms.

In some embodiments of Formula I-A, $R^{21a}$ and $R^{21b}$ are brought together with the carbon to which they are attached to form

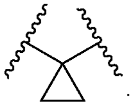 [SMILES: *C1(*)CC1]

In some embodiments of Formula I-A, $R^{21a}$ and $R^{21b}$ are brought together with the carbon to which they are attached to form

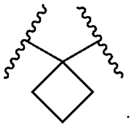 [SMILES: *C1(*)CCC1]
.

In some embodiments of Formula I-A, $R^{21a}$ and $R^{21b}$ are brought together with the carbon to which they are attached to form

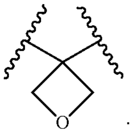 [SMILES: *C1(*)COC1]
.

In some embodiments of Formula I-A, $R^{21a}$ and $R^{21b}$ are brought together with the carbon to which they are attached to form

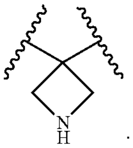 [SMILES: *C1(*)CNC1]
.

In some embodiments, the compound of Formula I-A is selected from a compound having the formula:

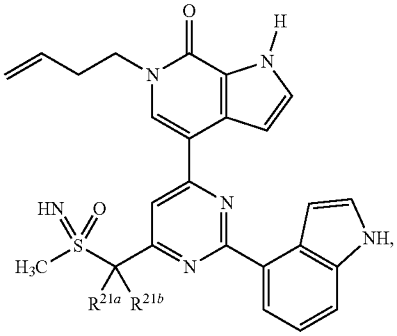

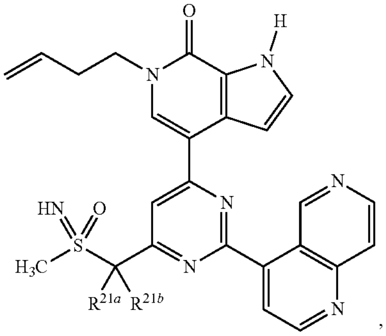
, or

-continued

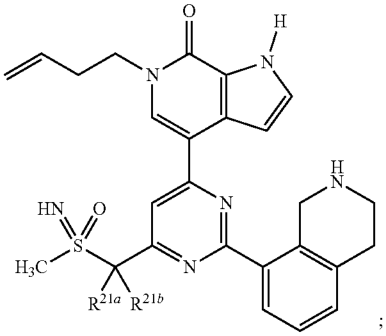
;

wherein $R^{21a}$ and $R^{21b}$ are as defined herein.

In some embodiments, the compound of Formula I-A is selected from a compound having the formula:

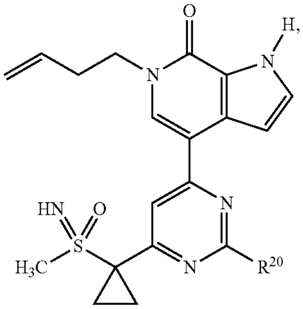

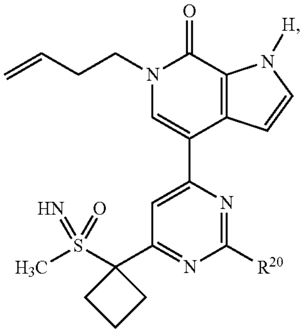

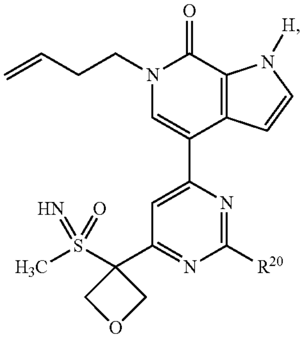
and

-continued
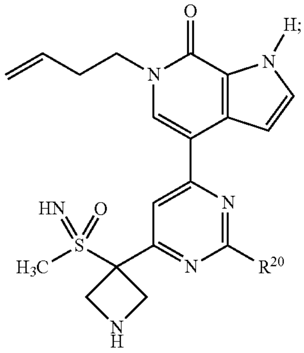
wherein $R^{20}$ is as defined herein.
Representative examples of compounds of Formula I include, but are not limited to:
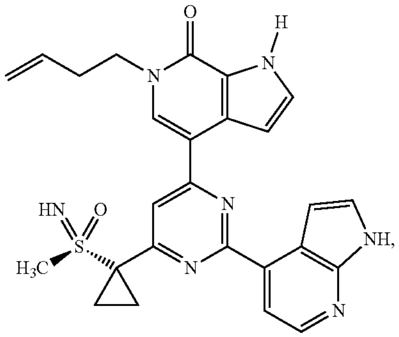
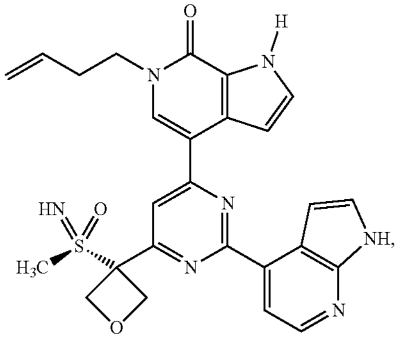
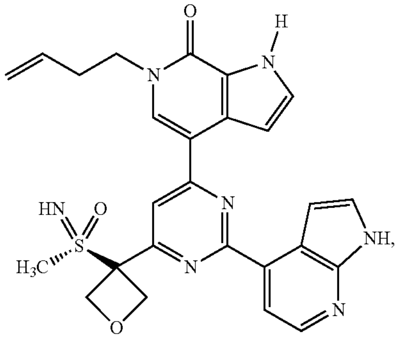
-continued
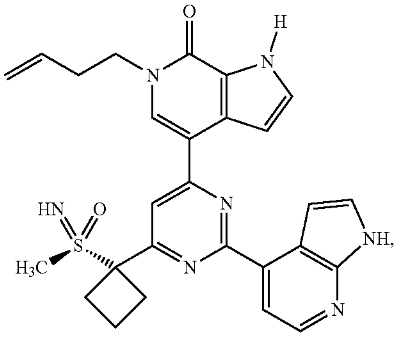
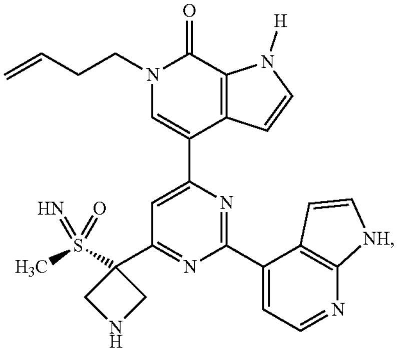
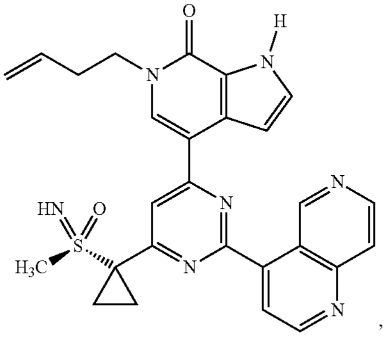
, and
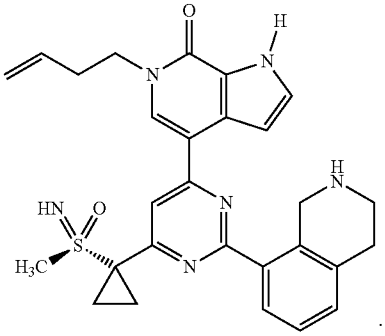
.

In some embodiments, the compound of Formula I may be a compound of Formula I-B:

(I-B)

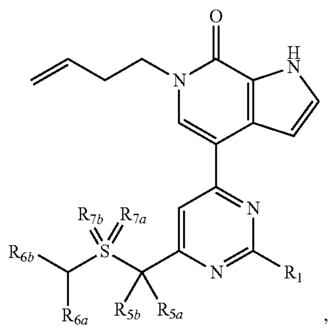

or a pharmaceutically acceptable salt thereof, wherein all variables are as defined herein.

In an alternative aspect, a compound of Formula II is provided:

(II)

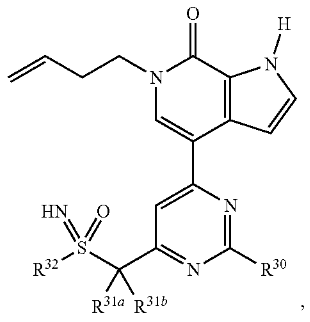

or a pharmaceutically acceptable salt thereof, wherein:

$R^{30}$ is selected from $R^{30a}$ or —NH—$R^{30a}$;

$R^{30a}$ is selected from unsubstituted or substituted aryl, unsubstituted or substituted heteroaryl, substituted or unsubstituted cycloalkyl, and unsubstituted or substituted heterocycloalkyl;

$R^{31a}$ and $R^{31b}$ are brought together with the carbon to which they are attached to form a substituted or unsubstituted cycloalkyl ring or a substituted or unsubstituted heterocycloalkyl ring;

$R^{32}$ is selected from $R^{32a}$ or —NH—$R^{32b}$;

$R^{32a}$ is selected from substituted or unsubstituted $C_1$-$C_6$ alkyl, substituted or unsubstituted aryl, substituted or unsubstituted cycloalkyl, substituted or unsubstituted heterocycloalkyl, —($C_1$-$C_6$ alkyl)-(substituted or unsubstituted aryl), —($C_1$-$C_6$ alkyl)-(substituted or unsubstituted heteroaryl), —($C_1$-$C_6$ alkyl)-(substituted or unsubstituted cycloalkyl), and —($C_1$-$C_6$ alkyl)-(substituted or unsubstituted heterocyloalkyl); and $R^{32b}$ is selected from hydrogen, substituted or unsubstituted $C_1$-$C_6$ alkyl, substituted or unsubstituted aryl, substituted or unsubstituted cycloalkyl, substituted or unsubstituted heterocycloalkyl, —($C_1$-$C_6$ alkyl)-(substituted or unsubstituted aryl), —($C_1$-$C_6$ alkyl)-(substituted or unsubstituted heteroaryl), —($C_1$-$C_6$ alkyl)-(substituted or unsubstituted cycloalkyl), and —($C_1$-$C_6$ alkyl)-(substituted or unsubstituted heterocyloalkyl).

In some embodiments of Formula II, $R^{30}$ is $R^{30a}$.

In some embodiments of Formula II, $R^{30}$ is NH—$R^{30a}$.

In some embodiments of Formula II, $R^{30a}$ can include a substituted aryl or a substituted or unsubstituted heteroaryl. For example, $R^{30a}$ can include a 5-, 6- and 7-membered aromatic ring. The ring can be a carbocyclic, heterocyclic, fused carbocyclic, fused heterocyclic, bicarbocyclic, or biheterocyclic ring system, which is optionally substituted as described herein. In some embodiments when $R^{20}$ is an heteroaryl, $R^{20}$ can include a monocyclic aromatic ring containing five or six ring atoms containing carbon and 1, 2, 3, or 4 heteroatoms each selected from non-peroxide oxygen, sulfur, and N(Y) where Y is absent or is H, O, ($C_1$-$C_5$) alkyl, phenyl or benzyl. Examples of aryl and heteroaryl rings include, but are not limited to, benzene, pyrrole, furan, thiophene, imidazole, oxazole, thiazole, triazole, pyrazole, pyridine, pyrazine, pyridazine and pyrimidine. The aromatic ring can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN.

In some embodiments of Formula II, $R^{30a}$ includes a polycyclic aryl or heteroaryl ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles, or both rings are aromatic. For example, in some embodiments when $R^{30a}$ is a heteroaryl, $R^{30a}$ can include an ortho-fused bicyclic heterocycle of about eight to ten ring atoms derived therefrom, particularly a benz-derivative or one derived by fusing a propylene, trimethylene, or tetramethylene diradical thereto. Examples of heteroaryl include, but are not limited to, furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

In specific examples of Formula II, $R^{30a}$ is selected from a substituted $C_5$-$C_6$ aryl or a substituted or unsubstituted $C_2$-$C_9$ heteroaryl. For example, $R^{30a}$ can be selected from a substituted phenyl, substituted or unsubstituted furyl, substituted or unsubstituted imidazolyl, substituted or unsubstituted triazolyl, substituted or unsubstituted triazinyl, substituted or unsubstituted oxazoyl, substituted or unsubstituted isoxazoyl, substituted or unsubstituted thiazolyl, substituted or unsubstituted isothiazoyl, substituted or unsubstituted pyrazolyl, substituted or unsubstituted pyrrolyl, substituted or unsubstituted pyrazinyl, substituted or unsubstituted tetrazolyl, substituted or unsubstituted pyridyl, substituted or unsubstituted thienyl, substituted or unsubstituted pyrimidinyl, substituted or unsubstituted indolyl, substituted or unsubstituted isoquinolyl, substituted or unsubstituted quinolyl, substituted or unsubstituted benzothienyl, substituted or unsubstituted benzofuranyl, substituted or unsubstituted benzoxazolyl, substituted or unsubstituted benzimidazoly, substituted or unsubstituted benzothiazolyl, substituted or unsubstituted isoindolyl, substituted or unsubstituted indolinyl, substituted or unsubstituted isoindolinyl, substituted or unsubstituted substituted or unsubstituted quinoxalinyl, substituted or unsubstituted quinazolinyl, substituted or unsubstituted cinnolinyl, substituted or unsubstituted [2,3-c] or [3,2-c]-thienopyridyl, and the like. In some examples, $R^{30a}$ is a substituted or unsubstituted fused $C_4$-$C_9$ heteroaryl, preferably unsubstituted indolyl.

In some embodiments of Formula II, $R^{30a}$ may be an unsubstituted or substituted heterocycloalkyl. Examples of heterocycloalkyls include, but are not limited to, saturated 4- to 7-membered monocyclic groups containing 1 to 4 nitrogen atoms [e.g., pyrrolidinyl, imidazolidinyl, piperidinyl, pyrrolinyl, azetidinyl, piperazinyl, and pyrazolidinyl]; saturated 4- to 6-membered monocyclic groups containing 1 to 2 oxygen atoms and 1 to 3 nitrogen atoms [e.g., morpholinyl]; and saturated 3- to 6-membered heteromonocyclic groups containing 1 to 2 sulfur atoms and 1 to 3 nitrogen atoms [e.g., thiazolidinyl]. Further examples of heterocycloalkyls include, but are not limited to, dihydrothienyl, dihydropyranyl, dihydrofuryl, and dihydrothiazolyl. Even further examples of heterocycloalkyls include, but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydroquinolyl, 2,3,4,4a,9,9a-hexahydro-1H-3-aza-fluorenyl, 5,6,7-trihydro-1,2,4-triazolo [3,4-a]isoquinolyl, 3,4-dihydro-2H-benzo[1,4]oxazinyl, benzo[1,4]dioxanyl, 2,3,-dihydro-1H-benzo[d]isothazol-6-yl, dihydropyranyl, dihydrofuryl, and dihydrothiazolyl.

In some embodiments of Formula II, $R^{30}$ is

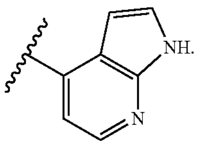 [SMILES: *c1ccnc2[nH]ccc12]

In some embodiments of Formula II, $R^{30}$ is

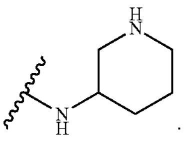

In some embodiments of Formula II, $R^{30}$ is

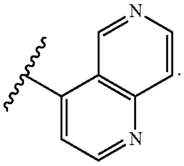

In some embodiments of Formula II, $R^{30}$ is

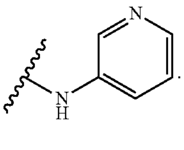

In some embodiments of Formula II, $R^{30}$ is

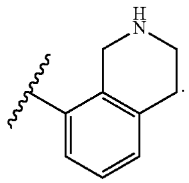 [SMILES: *c1cccc2c1CNCC2]

In some embodiments of Formula II, $R^{31a}$ and $R^{31b}$ may be brought together with the carbon to which they are attached to form a, unsubstituted or substituted cycloalkyl ring. For example, $R^{31a}$ and $R^{31b}$ may be brought together with the carbon to which they are attached to form a cyclopropyl ring, a cyclobutyl ring, a cyclopentyl ring, or a cyclohexyl ring. In particular embodiments, $R^{31a}$ and $R^{31b}$ may be brought together with the carbon to which they are attached to form a cyclopropyl ring or a cyclobutyl ring. In particular examples, $R^{31a}$ and $R^{31b}$ may be brought together with the carbon to which they are attached to form a cyclopropyl ring. The cycloalkyl ring can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN.

In some embodiments of Formula II, $R^{31a}$ and $R^{31b}$ may be brought together with the carbon to which they are attached to form an unsubstituted or substituted heterocycloalkyl ring containing at least one ring heteroatom (for example, 1 or 2 ring heteroatoms) selected from —O—, —N($Y^1$)—, and S, wherein $Y^1$ is hydrogen, $C_1$-$C_6$ alkyl, cycloalkyl, aryl, or heteroaryl. In particular embodiments, $R^{31a}$ and $R^{31b}$ may be brought together with the carbon to which they are attached to form a heterocycloalkyl ring containing 1 or 2 ring heteroatoms selected from —O— and —N($Y^1$)—. In particular embodiments, $R^{31a}$ and $R^{31b}$ may be brought together with the carbon atom to which they are attached to form a 3- to 6-membered heterocycloalkyl ring containing 1 or 2 ring oxygen atoms. In particular embodiments, $R^{31a}$ and $R^{31b}$ may be brought together with the carbon to which they are attached to form a 3- to 6-membered heterocycloalkyl ring containing 1 or 2 ring nitrogen atoms. The heterocycloalkyl ring can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN.

In some embodiments of Formula II, $R^{31a}$ and $R^{31b}$ are brought together with the carbon to which they are attached to form

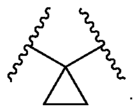 [SMILES: *C1(*)CC1]

In some embodiments of Formula II, $R^{31a}$ and $R^{31b}$ are brought together with the carbon to which they are attached to form

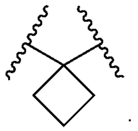 [SMILES: *C1(*)CCC1]

In some embodiments of Formula II, $R^{31a}$ and $R^{31b}$ are brought together with the carbon to which they are attached to form

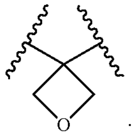 [SMILES: *C1(*)COC1]

In some embodiments of Formula II, $R^{31a}$ and $R^{31b}$ are brought together with the carbon to which they are attached to form

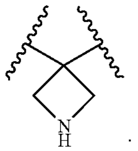 [SMILES: *C1(*)CNC1]

In some embodiments of Formula II, $R^{32}$ is $R^{32a}$.

In some embodiments of Formula II, $R^{32}$ is —NH—$R^{32b}$.

In some embodiments of Formula II, $R^{32a}$ is $C_1$-$C_6$ alkyl. In some embodiments of Formula II, $R^{32a}$ is selected from methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In particular embodiments of Formula II, $R^{32a}$ is methyl.

In some embodiments of Formula II, $R^{32a}$ is —($C_1$-$C_6$ alkyl)-(substituted or unsubstituted aryl). In particular embodiments of Formula II, $R^{32a}$ is —$CH_2$-(substituted or unsubstituted aryl). The aryl in $R^{32a}$ can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. In particular embodiments, $R^{32a}$ is —$CH_2$-(aryl substituted with amino). In particular embodiments, $R^{32a}$ is benzyl.

In some embodiments of Formula II, $R^{32b}$ is hydrogen.

In some embodiments of Formula II, $R^{32b}$ is —($C_1$-$C_6$ alkyl)-(substituted or unsubstituted aryl). In particular embodiments of Formula II, $R^{32b}$ is —$CH_2$-(substituted or unsubstituted aryl). The aryl in $R^{32b}$ can be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, amino, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, and —CN. In particular embodiments, $R^{32b}$ is —$CH_2$-(aryl substituted with amino) In particular embodiments, $R^{32b}$ is benzyl.

In some embodiments of Formula II, $R^{32}$ is

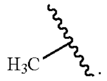

In some embodiments of Formula II, $R^{32}$ is

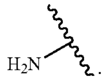

In some embodiments of Formula II, $R^{32}$ is

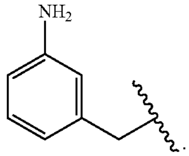 [SMILES: *Cc1cccc(N)c1]

In some embodiments of Formula II, $R^{32}$ is

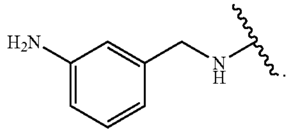 [SMILES: *NCc1cccc(N)c1]

Representative examples of compounds of Formula II include, but are not limited to:

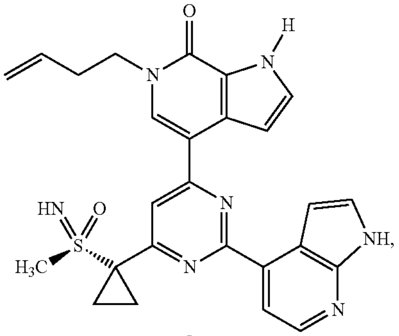

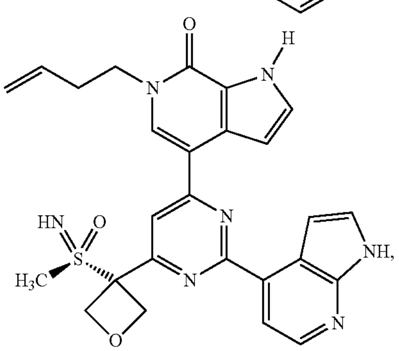

-continued
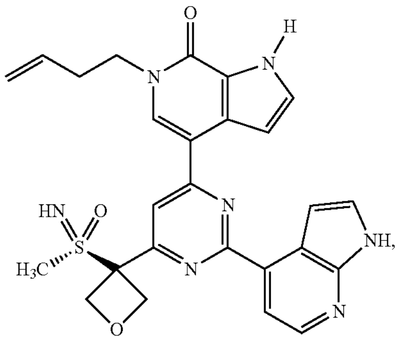
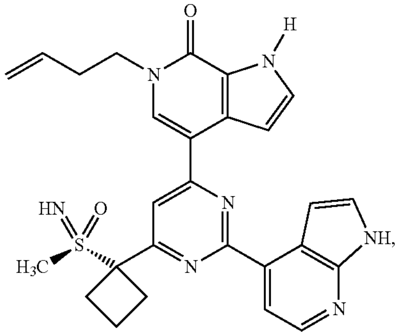
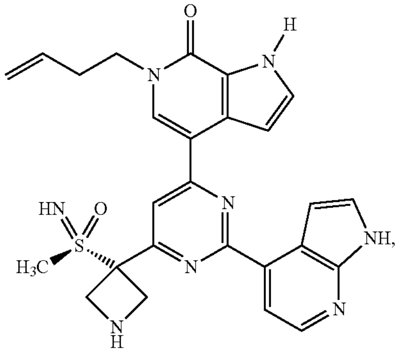
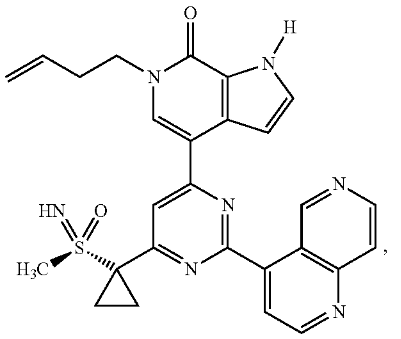
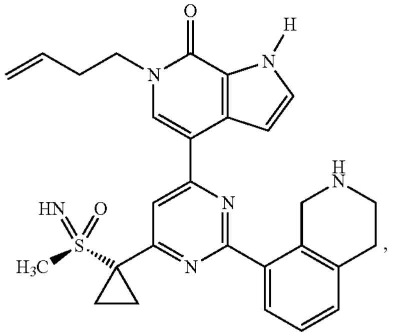
-continued
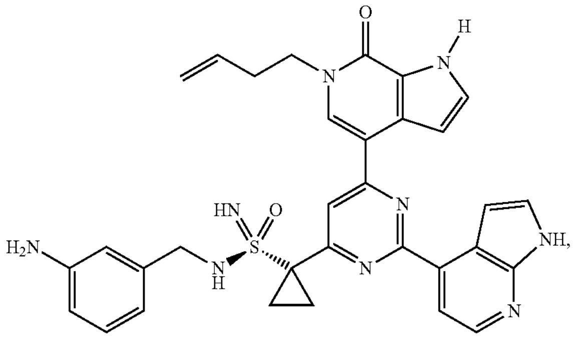
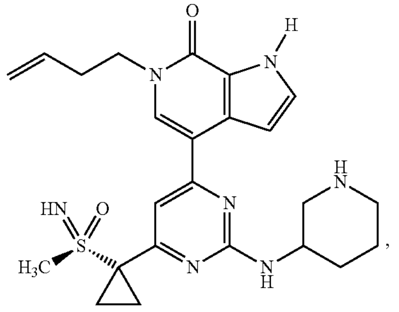
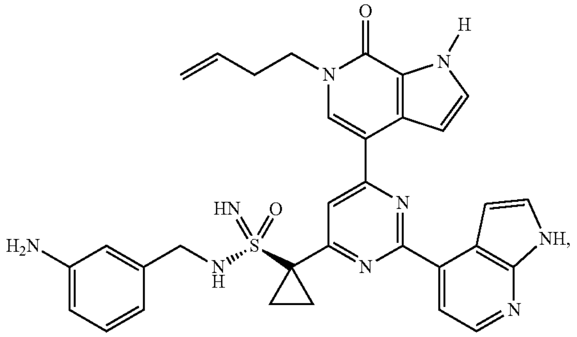
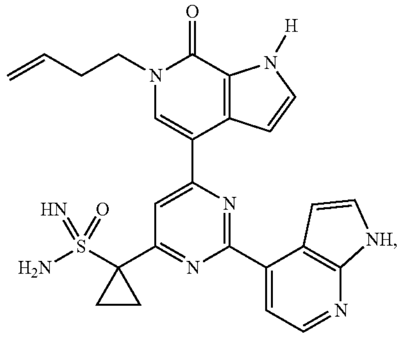
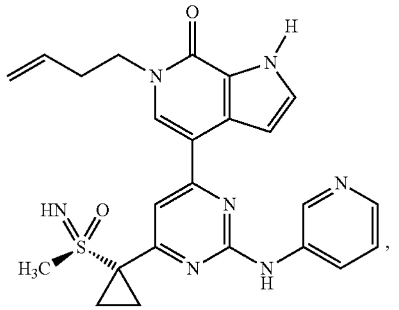

-continued

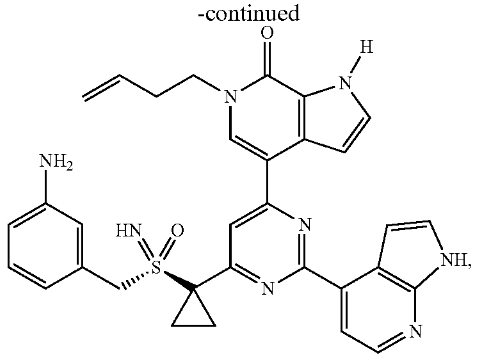

and

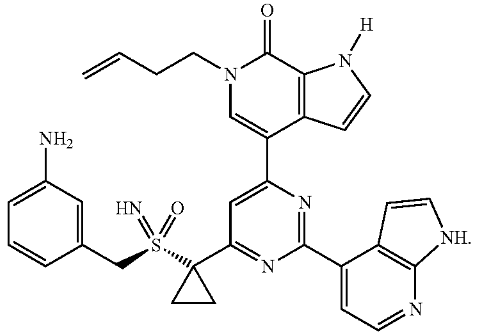

Methods

Further provided herein are methods of treating or preventing cancer in a subject, comprising administering to the subject an effective amount of a compound or composition as disclosed herein. The methods can further comprise administering a second compound or composition, such as, for example, anticancer agents or anti-inflammatory agents. Additionally, the method can further comprise administering an effective amount of ionizing radiation to the subject.

Methods of killing a tumor cell are also provided herein. The methods comprise contacting a tumor cell with an effective amount of a compound or composition as disclosed herein. The methods can further include administering a second compound or composition (e.g., an anticancer agent or an anti-inflammatory agent) or administering an effective amount of ionizing radiation to the subject.

Also provided herein are methods of radiotherapy of tumors, comprising contacting the tumor with an effective amount of a compound or composition as disclosed herein and irradiating the tumor with an effective amount of ionizing radiation.

Also disclosed are methods for treating oncological disorders in a patient. In one embodiment, an effective amount of one or more compounds or compositions disclosed herein is administered to a patient having an oncological disorder and who is in need of treatment thereof. The disclosed methods can optionally include identifying a patient who is or can be in need of treatment of an oncological disorder. The patient can be a human or other mammal, such as a primate (monkey, chimpanzee, ape, etc.), dog, cat, cow, pig, or horse, or other animals having an oncological disorder. Oncological disorders include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Other examples of cancers that can be treated according to the methods disclosed herein are adrenocortical carcinoma, adrenocortical carcinoma, cerebellar astrocytoma, basal cell carcinoma, bile duct cancer, bladder cancer, bone cancer, brain tumor, breast cancer, Burkitt's lymphoma, carcinoid tumor, central nervous system lymphoma, cervical cancer, chronic myeloproliferative disorders, colon cancer, cutaneous T-cell lymphoma, endometrial cancer, ependymoma, esophageal cancer, gallbladder cancer, gastric (stomach) cancer, gastrointestinal carcinoid tumor, germ cell tumor, glioma, hairy cell leukemia, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, myelogenous leukemia, nasal cavity and paranasal sinus cancer, nasopharyngeal cancer, neuroblastoma, non-small cell lung cancer, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, plasma cell neoplasm/multiple myeloma, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenström's macroglobulinemia, and Wilms' tumor.

In some aspect, disclosed are methods for treating a tumor or tumor metastases in a subject by the administration to the subject a combination of at least one compound or composition as disclosed herein and at least one cancer immunotherapeutic agent. The disclosed compounds can be administered alone or in combination with a cancer immunotherapeutic agent. The subject can receive the therapeutic compositions prior to, during or after surgical intervention to remove all or part of a tumor. Administration may be accomplished via direct immersion; systemic or localized intravenous (i.v.), intraperitoneal (i.p.), subcutaneous (s.c.), intramuscular (i.m.), or direct injection into a tumor mass; and/or by oral administration of the appropriate formulations.

In specific examples, the type of cancer is breast cancer or lung cancer.

In some embodiments, subject in need of treatment has been identified to have a high mitotic activity. In some embodiments, subject in need of treatment has been identified to have Mdm2-mediated degradation of the tumor suppressor p53. In some embodiments, subject in need of treatment has been identified to have decreased levels of the protooncogene cMYC.

Methods of inhibiting histone binding modules of TAF1 in at least one cell, comprising the step of contacting the at least one cell with an effective amount of a compound described herein are provided. Method for inhibiting a bromodomain of TAF1 in at least one cell, comprising the step of contacting the at least one cell with an effective amount of a compound described herein are also provided.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, Remington's Pharmaceutical Science by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane:sebacic acid] in a molar ratio (as used in GLIADEL); chondroitin; chitin; and chitosan.

For the treatment of oncological disorders, the compounds disclosed herein can be administered to a patient in need of treatment in combination with other antitumor or anticancer substances and/or with radiation and/or photodynamic therapy and/or with surgical treatment to remove a tumor. These other substances or treatments can be given at the same as or at different times from the compounds disclosed herein. For example, the compounds disclosed herein can be used in combination with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," Human Gene Therapy, 1999, 10(18):17).

Therapeutic application of compounds and/or compositions containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and compositions disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and compositions disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as compositions, in combination with a dermatologically acceptable carrier, which can be a solid or a liquid. Compounds and agents and compositions disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions disclosed herein can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions disclosed herein can be used in methods of treating cancer wherein the patient is to be treated or is or has been treated with mitotic inhibitors such as taxol or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, GLEEVEC (Novartis Pharmaceuticals Corporation) and HERCEPTIN (Genentech, Inc.), respectively. These other substances or radiation treatments can be given at the same as or at different times from the compounds disclosed herein. Examples of other suitable chemotherapeutic agents include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of suitable immunotherapeutic agents include, but are not limited to, alemtuzumab, cetuximab (ERBITUX), gemtuzumab, iodine 131 tositumomab, rituximab, trastuzamab (HERCEPTIN). Cytotoxic agents include, for example, radioactive isotopes (e.g., $I^{131}$, $I^{125}$, $Y^{90}$, $P^{32}$ etc.), and toxins of bacterial, fungal, plant, or animal origin (e.g., ricin, botulinum toxin, anthrax toxin, aflatoxin, jellyfish venoms (e.g., box jellyfish), etc.) Also disclosed are methods for treating an oncological disorder comprising administering an effective amount of a compound and/or agent disclosed herein prior to, subsequent to, and/or in combination with administration of a chemotherapeutic agent, an immunotherapeutic agent, a radiotherapeutic agent, or radiotherapy.

Kits

Kits for practicing the methods of the invention are further provided. By "kit" is intended any manufacture (e.g., a package or a container) comprising at least one reagent, e.g., anyone of the compounds described in Table 1. The kit may be promoted, distributed, or sold as a unit for performing the methods of the present invention. Additionally, the kits may contain a package insert describing the kit and methods for its use. Any or all of the kit reagents may be provided within containers that protect them from the external environment, such as in sealed containers or pouches.

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

Also disclosed are kits that comprise a composition comprising a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: AZD6738 and GNE371 Merged Scaffold

General Experimental

Reagents were purchased at the highest commercial quality and used without further purification, unless otherwise stated. All solvents were anhydrous unless otherwise stated. Anhydrous tetrahydrofuran (THF), 1,4-dioxane (dioxane), acetonitrile (ACN), toluene and dimethylformamide (DMF) were obtained by passing the previously degassed solvent through an activated alumina column (PPT Glass Contour Solvent Purification System). Yields refer to chromatographically and spectroscopically ($^1$H NMR) homogeneous material, unless otherwise stated. Reactions were monitored by LC-MS or thin layer chromatography (TLC) carried out on 250 μm SiliCycle SiliaPlates (TLC Glass-Backed TLC Extra Hard Layer, 60 Å), using shortwave UV light as the visualizing agent and p-anisaldehyde with heat as developing agents. Flash column chromatography was performed with a Biotage Isolera One (ZIP or SNAP Ultra cartridges) or with traditional glass flash columns using SiliCycle SiliaFlash® P60 (particle size 40-63 μm). NMR spectra were recorded on a Bruker Ascend™ 500 and 600 MHz instruments and were calibrated using residual undeuterated solvent as an internal reference ($CDCl_3$: 7.26 ppm $^1$H NMR, 77.16 ppm $^{13}$C NMR; MeOH-$d_4$: 3.31 ppm $^1$H NMR) The following abbreviations were used to explain NMR peak multiplicities: s=singlet, d=doublet, t=triplet, q=quartet, dd=doublet of doublet, tt=triplet of triplet, ddt=doublet of doublet of triplet, m=multiplet, br=broad. High-resolution mass spectra (HRMS) were recorded on an Agilent 6230 LC-MS TOF mass spectrometer.

Synthesis of GNE371 Fragment

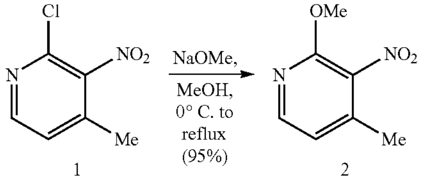 [SMILES: Cc1ccnc(Cl)c1[N+](=O)[O-] ; COc1nccc(C)c1[N+](=O)[O-]]

1 2

In a 500 mL round-bottomed flask equipped with a stir bar, septum capped addition funnel and argon balloon were added NaOMe (25.0 g, 464 mmol, 3.2 eq.) and MeOH (85 mL) then cooled to 0° C. A solution of 1 (25.0 g, 145 mmol, 1 eq.) in MeOH (150 mL) was added dropwise via additional funnel over 2 hours. The reaction mixture was then heated to reflux (78° C.) for 24 hours until full consumption of 1. The reaction was cooled to room temperature and the solvent was reduced via rotary evaporation to approximately 90 mL. Water (150 mL) was added and stirred for 3 minutes. The solid was filtered through a sintered glass funnel and washed with water (200 mL). The collected solid was dried under vacuum for 24 hours to give 2 (23.1 g, 137 mmol, 95% yield) as an off-white solid.

TLC: $R_f$=0.74 (20% EtOAc in hexanes)

$^1$H NMR: (600 MHz, $CDCl_3$) δ 8.10 (d, J=5.2 Hz, 1H), 6.82 (d, J=5.5 Hz, 1H), 4.01 (s, 3H), 2.33 (s, 3H) ppm.

$^{13}$C NMR: (151 MHz, $CDCl_3$) δ 155.19, 147.62, 141.56, 136.36, 118.95, 54.47, 16.88 ppm.

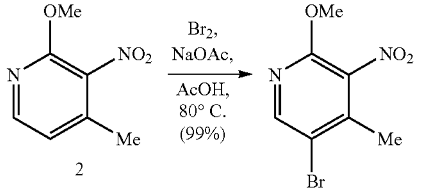

2 3

In a 500 mL round-bottomed flask equipped with a stir bar, septum capped addition funnel and argon balloon were added 2 (22.0 g, 131 mmol, 1 eq.), AcOH (131 mL) and NaOAc (38.6 g, 471 mmol, 3.6 eq.). A separate 200 mL round-bottomed flask containing 2M NaOH (100 mL) was connected to the addition funnel via cannula needle as a base trap for HBr formation. Br 2 (18.1 mL, 56.0 g, 351 mmol, 2.7 eq.) was transferred to the addition funnel then added dropwise over 30 minutes to the vigorously stirred suspension. The reaction was heated to 80° C. for 14 hours until full consumption of 2. The reaction was cooled to 0° C. and a 10% $Na_2SO_4$ solution (150 mL) was added followed by a saturated aqueous solution of $Na_2SO_4$ (150 mL) was added and stirred for 5 minutes. The precipitate was collected via filtration through a sintered glass funnel and washed with water (250 mL) then dried under vacuum to give 3 (32.0 g, 130 mmol, 99% yield) as a light-yellow solid.

TLC: $R_f$=0.88 (20% EtOAc in hexanes)

$^1$H NMR: (600 MHz, $CDCl_3$) δ 8.31 (s, 1H), 4.00 (s, 3H), 2.36 (s, 3H) ppm.

$^{13}$C NMR (151 MHz, $CDCl_3$) δ 154.18, 148.88, 140.94, 136.61, 114.55, 54.81, 17.80.

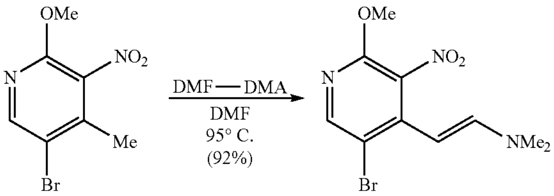

3 4

In a 500 mL round-bottomed flask equipped with a stir bar and addition funnel was added 3 (22 g, 89 mmol, 1 eq.) and DMF (178 mL) then heated to 80° C. DMF-DMA (104 mL, 736 mmol, 8.26 eq.) was added via addition funnel over 5 minutes then heated to 95° C. for 9 hours until full consumption of 3. The reaction was cooled to room temperature then poured into 500 mL of ice-cold water (red solid crashed out). The solid was filtered through a sintered glass funnel while rinsing with ice-cold water (100 mL) and the collected solid was dried under vacuum to give 4 (24.8 g, 82.0 mmol, 92% yield) as a red solid.

TLC: $R_f$=0.62 (20% EtOAc in hexanes)

$^1$H NMR: (600 MHz, $CDCl_3$) δ 8.11 (s, 1H), 6.99 (d, J=13.7 Hz, 1H), 4.91 (d, J=13.6 Hz, 1H), 3.94 (s, 3H), 2.91 (s, 7H) ppm.

$^{13}$C NMR: (151 MHz, $CDCl_3$) δ 154.66, 148.20, 147.21, 139.78, 131.36, 111.69, 87.60, 54.39, 40.52 ppm.

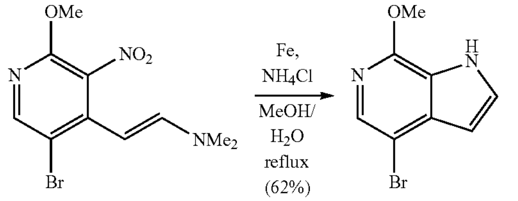

4 5

In a 1 L round-bottomed flask equipped with a stir bar, septum capped reflux condenser and argon balloon were added $Fe^0$ (20.0 g, 358 mmol, 10.8 eq.), $NH_4Cl$ (20.0 g, 374 mmol, 11.3 eq.) and water (50 mL). 4 (10.0 g, 33.1 mmol, 1 eq.) and MeOH (380 mL) were added then heated to 90° C. for 38 hours. The reaction mixture was carefully filtered while hot through a pad of Celite in a sintered glass funnel while rinsing with MeOH (3× mL). The filtrate was concentrated to give a crude residue that was taken up in EtOAc (300 mL) and water (250 mL). The aqueous layer was extracted with EtOAc (4×150 mL), combined organic layers were dried over $Na_2SO_4$, filtered and adsorbed to silica gel. Further purification by silica gel column chromatography using hexanes/EtOAc (0% to 20% EtOAc gradient in hexanes) to give 5 (4.66 g, 20.5 mmol, 62% yield) as a yellow solid.

TLC: $R_f$=0.35 (20% EtOAc in hexanes)

$^1$H NMR: (600 MHz, $CDCl_3$) δ 8.84 (s, 1H), 7.84 (s, 1H), 7.31 (t, J=2.8 Hz, 1H), 6.57 (dd, J=3.1, 2.2 Hz, 1H), 4.08 (s, 3H) ppm.

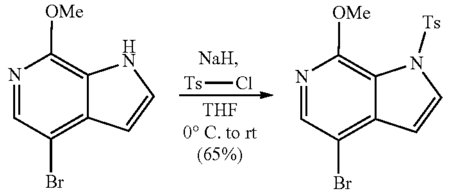

5 6

In a 250 mL septum capped round-bottomed flask equipped with a stir bar and argon balloon were added NaH (1.91 g, 47.6 mmol, 3.2 eq., 60%) and THF (70 mL) then cooled to 0° C. A solution of 5 (3.38 g, 14.9 mmol, 1 eq.) in THF (70 mL) was added via cannula transfer. After addition of 5, the reaction was warmed to room temperature where it stirred for 1 hour then cooled to 0° C. A solution of Ts-Cl (3.77 g, 19.8 mmol, 1.33 eq.) in THF (70 mL) was added via cannula transfer. The reaction mixture was warmed to room temperature where it stirred for 2 hours. The reaction was quenched with saturates aqueous $NH_4Cl$ (120 mL) then extracted with EtOAc (4×60 mL). The combined organic layers were dried over $Na_2SO_4$, filtered and adsorbed to silica gel. Further purification by silica gel column chromatography using hexanes/EtOAc (0% to 10% EtOAc in hexanes) to give 6 (3.7 g, 9.71 mmol, 65% yield) as a light brown solid.

TLC: $R_f$=0.53 (20% EtOAc in hexanes)

$^1$H NMR: (600 MHz, $CDCl_3$) δ 7.97 (d, J=3.6 Hz, 1H), 7.89 (s, 1H), 7.77 (d, J=8.4 Hz, 2H), 7.27 (d, J=7.9 Hz, 2H), 6.67 (d, J=3.6 Hz, 1H), 3.88 (s, 3H), 2.38 (s, 3H) ppm.

$^{13}$C NMR: (151 MHz, $CDCl_3$) δ 150.47, 145.27, 139.35, 139.22, 135.91, 131.14, 129.58, 127.92, 119.24, 106.05, 104.88, 53.28, 21.67 ppm.

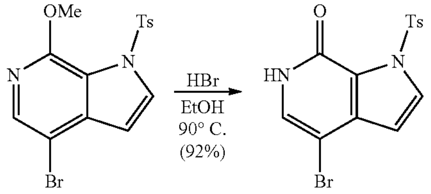

6 7

In a 40 mL septum capped reaction vial equipped with a stir bar were added 6 (1.30 g, 3.41 mmol, 1 eq.) and EtOH (5.5 mL). HBr (11.6 mL, 102 mL, 30 eq., 48% in water) was added via syringe. The reaction mixture was heated to 90° C. for 2 hours then cooled to 0° C. (white precipitate formed). The solid was filtered using a sintered glass funnel washing with ice-cold water (30 mL) then dried under vacuum to give 7 (1.15 g, 3.13 mmol, 92% yield) as a white solid.

$^1$H NMR: (600 MHz, DMSO-$d_6$) δ 11.50 (s, 1H), 8.04 (d, J=3.5 Hz, 1H), 7.94 (d, J=8.4 Hz, 2H), 7.41 (d, J=8.0 Hz, 2H), 7.35 (s, 1H), 6.60 (d, J=3.5 Hz, 1H), 2.37 (s, 3H) ppm.

$^{13}$C NMR: (151 MHz, DMSO) δ 152.48, 145.87, 137.20, 135.49, 131.63, 130.11, 130.09, 128.87, 122.31, 106.74, 91.76, 21.59 ppm.

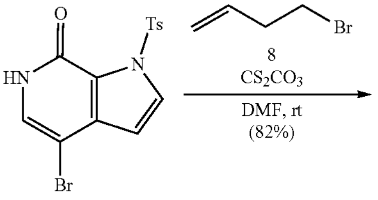

7

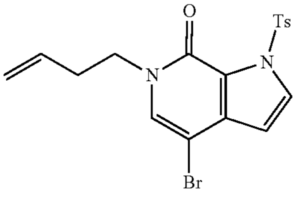

9

In a 40 mL septum capped reaction vial equipped with a stir bar were added 7 (1.05 g, 2.86 mmol, 1 eq.) and DMF (16 mL). $Cs_2CO_3$ (1.86 g, 5.72 mmol, 2 eq.) followed by 8 (0.502 g, 0.377 mL, 3.72 mmol, 1.3 eq.) were added. The reaction stirred at room temperature for 6 hours. The reaction mixture was filtered through a pad of Celite in a sintered glass funnel rinsing with EtOAc (30 mL). The filtrate was concentrated and the crude was taken up in EtOAc (30 mL) and water (25 mL) then extracted with EtOAc (4×30 mL). Combined organic layers were dried over $Na_2SO_4$, filtered and concentrated. Further purification by silica gel column chromatography using hexanes/EtOAc (0% to 15% EtOAc in hexanes) provided 9 (0.988 g, 2.34 mmol, 82% yield) as a clear colorless oil.

TLC: $R_f$=0. (20% EtOAc in hexanes)

$^1H$ NMR: (600 MHz, $CDCl_3$) δ 7.98 (d, J=8.4 Hz, 2H), 7.91 (d, J=3.5 Hz, 1H), 7.28 (d, J=7.7 Hz, 2H), 7.12 (s, 1H), 6.49 (d, J=3.5 Hz, 1H), 5.70 (ddt, J=18.2, 9.5, 6.9 Hz, 1H), 5.00 (s, 1H), 4.99-4.96 (m, 1H), 3.94 (t, J=7.3 Hz, 2H), 2.43-2.40 (m, 2H), 2.39 (s, 3H) ppm.

$^{13}C$ NMR: (151 MHz, $CDCl_3$) δ 152.13, 145.10, 136.61, 135.73, 133.85, 131.92, 131.01, 129.47, 128.73, 122.58, 117.85, 106.12, 92.69, 48.76, 33.67, 21.70 ppm.

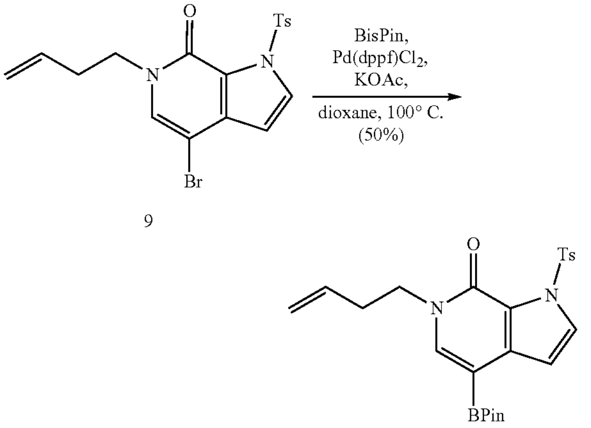

9

10

In a flame dried septum capped 1-dram reaction vial equipped with a stir bar and argon balloon were added 9 (0.10 g, 0.24 mmol, 1 eq.) and dioxane (1.2 mL). BisPin (0.066 g, 0.26 mmol, 1.1 eq.), KOAc (0.047 g, 0.475 mmol, 2 eq.) and $Pd(dppf)Cl_2$ (8.7 mg, 0.012 mmol, 0.05 eq.) were added. The resulting mixture was degassed under vacuum and sonication followed by purging with argon (3 cycles). The reaction mixture was heated to 100° C. for 15 hours then cooled to room temperature. The reaction mixture was diluted with EtOAc (20 mL) and filtered through a pad of Celite in a sintered glass funnel while rinsing with EtOAc (20 mL). The filtrate was concentrated and purified by silica gel column chromatography using hexanes/EtOAc (0% to 20% EtOAc in hexanes) to give 10 (0.056 g, 0.120 mmol, 50% yield) as a clear colorless oil that was used in the next step without further characterization.

LRMS: $[M+H^+]$=469.1

Synthesis of AZD6738 Fragment

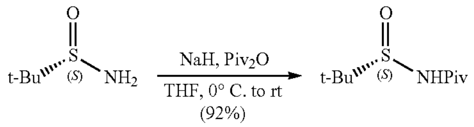

11 12

In a flame dried 1 L round-bottomed flask equipped with a stir bar, septum capped addition funnel and argon balloon were added 1 (5.21 g, 42.9 mmol, 1.1 eq.) and THF (243 mL) then cooled to 0° C. Once cool, NaH (5.2 g, 98 mmol, 60% wt, 2.5 eq.) was added and stirred at 0° C. for 15 minutes before warming to room temperature. A solution of $Piv_2O$ (7.26 g, 7.91 mL, 39.1 mmol, 1 eq.) in THF (147 mL) was added dropwise over 75 minutes at room temperature. Once addition was complete, the reaction stirred for an additional 20 minutes before quenching with MeOH (20 mL) followed by brine (100 mL) and saturated aqueous $NH_4Cl$ (100 mL). The aqueous layer was extracted with EtOAc (4×150 mL), combined organic layers were washed with saturated aqueous $NaHCO_3$ (100 mL) and brine (100 mL), dried over $Na_2SO_4$, filtered and concentrated. The crude material was adsorbed to silica gel and purified by silica gel column chromatography using DCM/EtOAc (5:1 isocratic) to give 13 (7.36 g, 35.8 mmol, 92% yield) as a white solid.

TLC: $R_f$=0.5 (DCM/EtOAC, 5:1, p-anisaldehyde stain).

$^1H$ NMR: (500 MHz, $CDCl_3$) δ 7.31 (s, 1H), 1.24 (s, 9H), 1.23 (s, 9H) ppm.

$^{13}C$ NMR: (126 MHz, $CDCl_3$) δ 178.84, 57.40, 39.99, 27.22, 22.06 ppm.

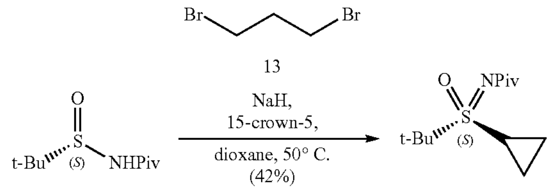

12 14

In a flamed dried 500 mL septum capped round-bottomed flask equipped with a stir bar were added 13 (5.50 g, 26.8 mmol, 1 eq.) and dioxane (268 mL). 15-crown-5 ether (6.36 mL, 32.2 mmol, 1.2 eq.) was added followed by NaH (1.29 g, 32.2 mmol, 60% wt, 1.2 eq). The reaction mixture stirred at room temperature for 1 hour then 14 (3.28 mL, 32.2 mmol, 1.2 eq.) was added via syringe where it stirred at room temperature for an additional 20 minutes before heating to 50° C. for 15 hours. The reaction was cooled to room temperature and additional NaH (1.29 g, 32.2 mmol, 1.2 eq) was added. The reaction was heated to 50° C. for 15 hours then cooled to room temperature where it was quenched with saturated aqueous $NH_4Cl$ (100 mL) and water (100 mL). The aqueous layer was extracted with EtOAc (4×100 mL), combined organic layers were dried over $Na_2SO_4$, filtered and concentrated. Further purification by silica gel column chromatography using hexanes/EtOAc (0% to 20% EtOAc in hexanes) provided 15 (2.76 g, 11.3 mmol, 42% yield) as a white solid.

TLC: $R_f$=0.33 (40% EtOAc in hexanes)

$^1H$ NMR: (500 MHz, $CDCl_3$) δ 2.51-2.43 (m, 1H), 1.63-1.56 (m, 1H), 1.49 (s, 8H), 1.31-1.23 (m, 1H), 1.17 (s, 10H), 1.12-1.07 (m, 1H) ppm.

$^{13}C$ NMR: (126 MHz, $CDCl_3$) δ 186.93, 62.82, 41.87, 27.91, 23.93, 23.86, 6.60, ppm.

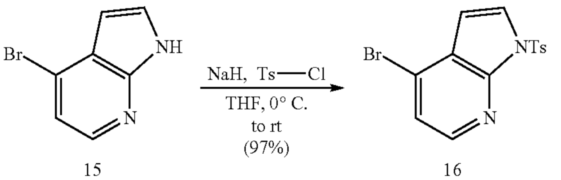

15 16

In a flame dried 500 mL septum capped round-bottomed flask equipped with a stir bar were added (6.20 g, 31.5 mmol, 1 eq.) and THF (157 mL) then cooled to 0° C. NaH (1.51 g, 37.8 mmol, 1.2 eq.) was added portion-wise and stirred at 0° C. for 30 minutes followed by the addition of Ts-Cl (6.60 g, 34.6 mmol, 1.1 eq.) in one portion. The reaction mixture was stirred at 0° C. for 1 hour then warmed to room temperature where it stirred for 3 hours. The reaction was quenched with saturated aqueous $NH_4Cl$ (125 mL), extracted with EtOAc (3×150 mL), dried over $Na_2SO_4$, filtered and concentrated. The crude solid was adsorbed to silica gel and filtered through a short plug of silica gel rinsing with hexanes (200 mL) then elution with (20% EtOAc in hexanes) to give 17 (10.7 g, 30.5 mmol, 97% yield) as a light-yellow solid.

TLC: $R_f$=0.29 (10% EtOAc in hexanes)

$^1$H NMR: (500 MHz, $CDCl_3$) δ 8.22 (d, J=5.3 Hz, 1H), 8.06 (d, J=8.4 Hz, 2H), 7.78 (d, J=4.0 Hz, 1H), 7.35 (d, J=5.2 Hz, 1H), 7.27 (d, J=8.7 Hz, 2H), 6.63 (d, J=4.1 Hz, 1H), 2.37 (s, 3H) ppm.

$^{13}$C NMR: (126 MHz, $CDCl_3$) δ 146.73, 145.53, 145.02, 135.06, 129.74, 128.14, 126.96, 125.70, 124.35, 122.05, 104.86, 21.68 ppm.

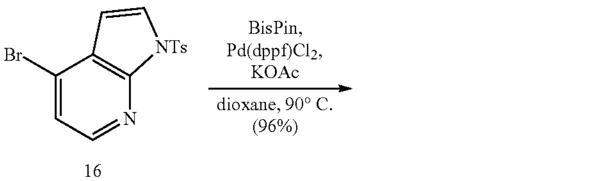

16

17

In a 250 mL septum capped round-bottomed flask equipped with a stir bar were added 17 (5.04 g, 14.4 mmol, 1 eq.), BisPin (5.10 g, 20.1 mmol, 1.4 eq.) and dioxane (72 mL). $Pd(dppf)Cl_2$ (0.525 g, 0.718 mmol, 0.05 eq.) and KOAc (2.82 g, 28.7 mmol, 2 eq.) were added and the reaction was heated to 90° C. for 52 hours. The reaction was cooled to room temperature and filtered through a pad of Celite in a sintered glass funnel. The filtrate was concentrated and adsorbed to silica gel. Purification by silica gel column chromatography using hexanes/EtOAc (0% to 10% EtOAc) provided 18 (5.51 g, 13.8 mmol, 96% yield) as a white solid.

TLC: $R_f$=0.18 (5% MeOH in DCM)*17 decomposes on TLC to boronic acid.

$^1$H NMR: (500 MHz, $CDCl_3$) δ 8.42 (d, J=4.7 Hz, 1H), 8.02 (d, J=8.4 Hz, 2H), 7.74 (d, J=4.0 Hz, 1H), 7.52 (d, J=4.7 Hz, 1H), 7.23 (d, J=8.1 Hz, 2H), 7.01 (d, J=4.0 Hz, 1H), 2.33 (s, 3H), 1.35 (s, 12H) ppm.

$^{13}$C NMR: (126 MHz, $CDCl_3$) δ 146.91, 145.00, 144.08, 135.53, 129.58, 128.01, 127.89, 127.37, 126.76, 124.56, 107.36, 84.41, 24.95, 21.61 ppm.

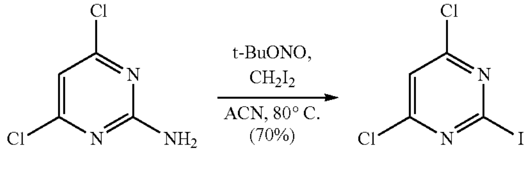

18 19

In a 500 mL round-bottomed flask equipped with a stir bar, septum capped reflux condenser and argon balloon were added 19 (10 g, 61 mmol, 1 eq.), ACN (86 mL) and $CH_2I_2$ (5.41 mL, 67.1 mmol, 1.1 eq.). To the stirring solution, t-BuONO (40.3 mL, 305 mmol, 5 eq., 90%) was added via syringe and resulting reaction mixture was heated to 80° C. for 4 hours. The reaction was cooled to room temperature and the solvents were removed under vacuum. The crude residue was taken up in EtOAc (450 mL) and washed with saturated aqueous $Na_2SO_3$ (3×150 mL). The combined aqueous layers were back extracted with EtOAc (2×150 mL) and combined with the first organic layer. The combined organic layers were dried over $Na_2SO_4$ then filtered and adsorbed to silica gel. Further purification by silica gel column chromatography using hexanes and EtOAc (0% to 10% EtOAc) provided 20 (11.7 g, 42.7 mmol, 70% yield) as an off-white solid.

TLC: $R_f$=0.58 (10% EtOAc in hexanes)

$^1$H NMR: (500 MHz, $CDCl_3$) δ 7.39 (s, 1H) ppm.

$^{13}$C NMR: (126 MHz, $CDCl_3$) δ 161.04, 125.97, 120.87 ppm.

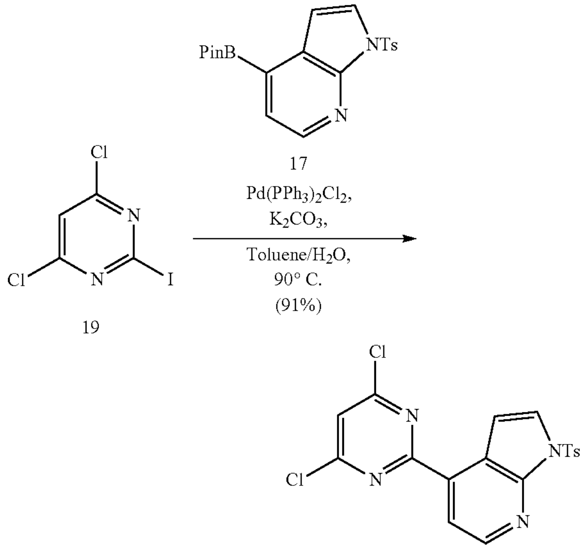

17

19

20

In a 20 mL septum capped vial equipped with a stir bar and argon balloon were added 20 (0.450 g, 1.64 mmol, 1 eq.), 18 (0.652 g, 1.64 mmol) and toluene/water (13.5 mL/0.135 mL, 100:1). $K_2CO_3$ and $Pd(PPh_3)_2Cl_2$ were added and the reaction mixture was heated to 90° C. for 34 hours. The reaction was cooled to room temperature and diluted with EtOAc (50 mL) and water (15 mL). The aqueous layer was extracted with EtOAc (4×25 mL) and DCM (2×25 mL). The combined organic layers were dried over $Na_2SO_4$, filtered and adsorbed to silica gel. Purification by silica gel column chromatography using hexanes/DCM (10% to 70% DCM in hexanes) provided 21 (0.625 g, 1.49 mmol, 91% yield) as a white solid.

TLC: $R_f$=0.516 (66% DCM in hexanes)

$^1H$ NMR: (500 MHz, $CDCl_3$) δ 8.56 (d, J=5.1 Hz, 1H), 8.19 (d, J=5.1 Hz, 1H), 8.08 (d, J=8.5 Hz, 2H), 7.89 (d, J=4.0 Hz, 1H), 7.59 (d, J=4.0 Hz, 1H), 7.37 (s, 1H), 7.30-7.26 (m, 2H), 2.37 (s, 3H) ppm.

$^{13}C$ NMR: (126 MHz, $CDCl_3$) δ 164.42, 162.16, 148.72, 145.34, 144.89, 135.27, 134.88, 129.67, 128.24, 128.15, 121.35, 120.02, 118.37, 106.78, 21.66 ppm.

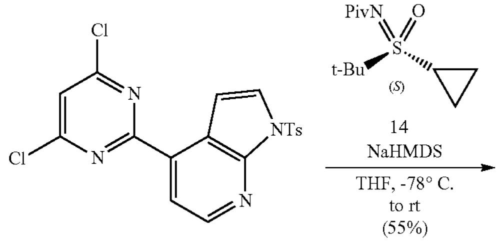

20

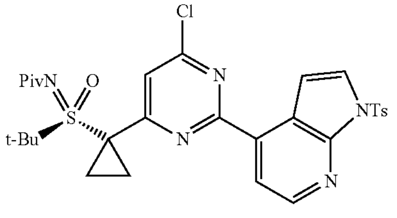

21

In a flame dried 500 mL septum capped round-bottomed flask equipped with a stir bar and argon balloon were added 21 (1.90 g, 4.53 mmol, 1 eq.), 15 (1.11 g, 4.53 mmol, 1 eq.) and THF (181 mL) then cooled to −78° C. NaHMDS (2.72 mL, 5.44 mmol, 1.2 eq., 2M in THF) was added via syringe and stirred at −78° C. for 10 hours. Additional NaHMDS (0.60 mL, 1.2 mmol, 0.26 eq., 2M in THF) was added and continued to stir at −78° C. for 2 hours. The reaction was quenched with saturated aqueous $NH_4Cl$ (100 mL) while still at −78° C. The aqueous layer was extracted with EtOAc (3×100 mL), combined organic layers were dried over $Na_2SO_4$, filtered and concentrated. The crude residue was adsorbed to silica gel and further purified by silica gel column chromatography using hexanes/EtOAc (0% to 20% EtOAc in hexanes) to give 22 (1.56 g, 2.48 mmol, 55% yield) as light-yellow waxy solid.

TLC: $R_f$=0.54 (40% EtOAc in hexanes)

$^1H$ NMR: (500 MHz, $CDCl_3$) δ 8.58 (d, J=5.1 Hz, 1H), 8.20 (d, J=5.1 Hz, 1H), 8.09 (d, J=8.4 Hz, 2H), 7.90 (d, J=4.0 Hz, 1H), 7.72 (s, 1H), 7.58 (d, J=4.0 Hz, 1H), 7.28 (dd, J=8.6, 0.8 Hz, 2H), 2.57 (ddd, J=10.6, 8.1, 6.0 Hz, 1H), 2.37 (s, 3H), 2.14-2.06 (m, 1H), 1.98 (ddd, J=10.5, 7.8, 5.6 Hz, 1H), 1.42-1.40 (m, 1H), 1.38 (s, 9H), 1.25 (s, 9H) ppm.

$^{13}C$ NMR: (126 MHz, $CDCl_3$) δ 188.09, 166.14, 163.75, 162.20, 148.73, 145.40, 144.94, 135.66, 135.22, 129.69, 128.19, 128.13, 123.22, 121.23, 118.12, 106.64, 66.72, 42.29, 27.78, 24.96, 24.65, 21.69, 16.78, 14.73 ppm.

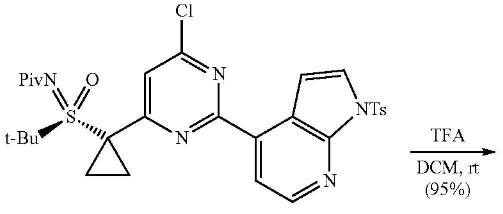

21

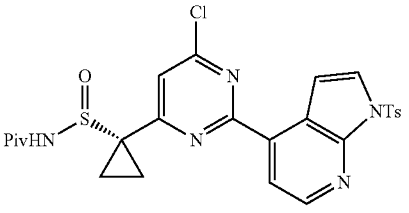

22

In a 40 mL septum capped reaction vial equipped with a stir bar and argon balloon were added 22 (1.52 g, 2.42 mmol, 1 eq.) and DCM (24 mL). TFA (0.205 mL, 2.66 mmol, 1.1 eq.) was added and the reaction stirred at room temperature for 4 hours. The reaction was quenched with saturated aqueous $NaHCO_3$ (40 mL) and the aqueous layer was extracted with DCM (3×40 mL), combined organic layers were dried over $Na_2SO_4$, filtered and concentrated. Further purification by silica gel column chromatography using hexanes/EtOAc (10% to 50% EtOAc in hexanes) to give 23 (1.31 g, 2.29 mmol, 95% yield) as an opaque oil.

TLC: $R_f$=0.16 (40% EtOAc in hexanes)

$^1H$ NMR: (500 MHz, $CDCl_3$) δ 8.57 (d, J=5.1 Hz, 1H), 8.30 (s, 1H), 8.13 (d, J=5.1 Hz, 1H), 8.11-8.05 (m, 2H), 7.89 (d, J=4.0 Hz, 1H), 7.50 (d, J=4.0 Hz, 1H), 7.34 (s, 1H), 7.28 (dd, J=8.7, 0.7 Hz, 2H), 2.37 (s, 3H), 1.92 (ddd, J=10.2, 7.2, 5.3 Hz, 1H), 1.72 (ddd, J=9.4, 7.2, 5.3 Hz, 1H), 1.65 (ddd, J=10.3, 7.2, 5.5 Hz, 1H), 1.51 (ddd, J=9.5, 7.2, Hz, 1H), 0.99 (s, 9H) ppm.

$^{13}C$ NMR: (126 MHz, $CDCl_3$) δ 178.71, 166.04, 164.07, 162.70, 148.69, 145.39, 144.91, 135.63, 135.25, 129.69, 128.30, 128.14, 121.21, 119.69, 118.32, 106.58, 44.80, 39.60, 26.94, 21.66, 13.93, 10.62 ppm.

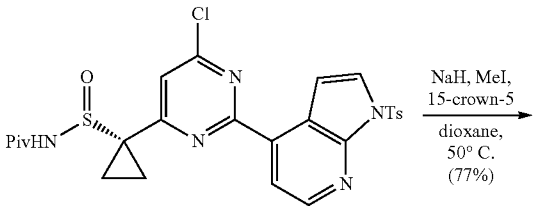

22

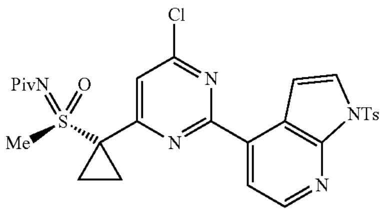

23

In a 20 mL septum capped vial equipped with a stir bar and argon balloon were added 23 (0.190 g, 0.332 mmol, 1 eq.), dioxane (3.3 mL) and 15-crown-5 ether (0.079 mL, 0.399 mmol, 1.2 eq.). NaH (0.016 g, 0.399 mmol, 1.2 eq., 60% wt) was added and the reaction mixture stirred at room temperature for 20 minutes. MeI (0.042 ml, 0.664 mmol, 2 eq.) was added and the reaction was heated to 50° C. for 24 hours. The reaction was cooled to room temperature and quenched with saturated aqueous $NH_4Cl$ (10 mL) and water (5 mL). The aqueous layer was extracted with EtOAc (4×20 mL), combined organic layers were dried over $Na_2SO_4$, filtered and concentrated. Further purification by silica gel column chromatography using hexanes/EtOAc (0% to 30% EtOAc in hexanes) provided 24 (0.150 g, 0.256 mmol, 77% yield) as a light-yellow oil.

TLC: $R_f$=0.41 (40% EtOAc in hexanes)

LRMS: [M+H$^+$]=586.0

Convergent Coupling of Both Fragments:

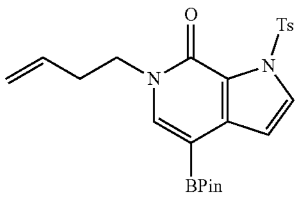

10

+

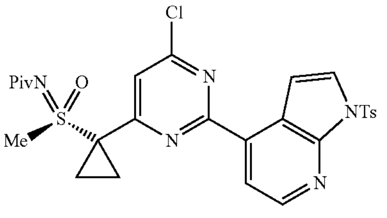

23

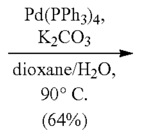

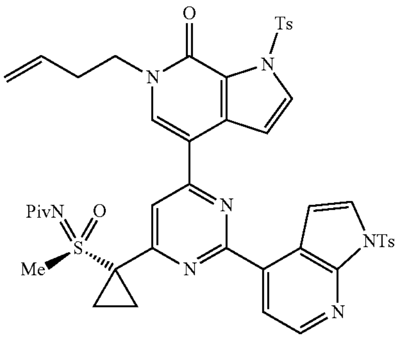

24

In a 1-dram septum capped reaction vial equipped with a stir bar and argon balloon were added 23 (0.032 g, 0.055 mmol, 1 eq.), 10 (0.031 g, 0.066 mmol, 1.2 eq.), dioxane (0.6 mL) and water (0.038 mL). $K_2CO_3$ (0.015 g, 0.109 mmol, 2 eq.) and $Pd(PPh_3)_4$ were added. The resulting reaction mixture was degassed under vacuum and sonicated followed by purging with argon (3 cycles) then heated to 90° C. for 3 hours. The reaction was cooled to room temperature and diluted with EtOAc (20 mL) and filtered through a pad of Celite in a sintered glass funnel. The filtrate was concentrated and purified by silica gel column chromatography using hexanes/EtOAc (10% to 60% EtOAc in hexanes) to give 24 (0.031 g, mmol, 64% yield) as a clear colorless oil.

TLC: $R_f$=0.47 (60% EtOAc in hexanes)

LRMS: [M+H$^+$]=892.1

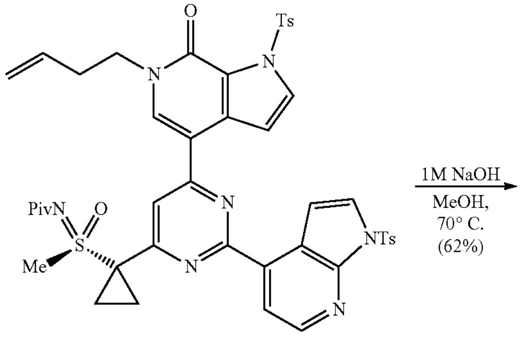

24

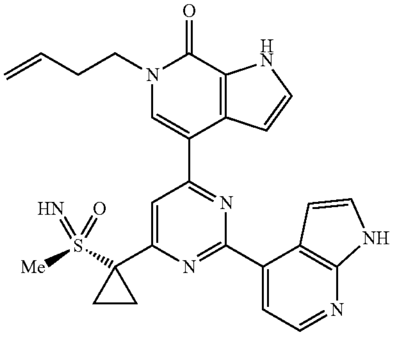

25

In a 1-dram septum capped reaction vial equipped with a stir bar were added 24 (0.023 g, 0.026 mmol, 1 eq.) and MeOH (0.258 mL). An aqueous 1M NaOH solution (0.258 mL, 0.258 mmol, 10 eq.) was added and the reaction was heated to 70° C. for 14 hours. The reaction was cooled to room temperature and quenched with saturated aqueous $NH_4Cl$ (3 mL) and water (5 mL) the extracted with EtOAc (4×15 mL). The combined organic layers were dried over $Na_2SO_4$, filtered and concentrated. Further purification by silica gel column chromatography using DCM/MeOH (0% to 5% MeOH in DCM) to provide 25 (8.1 mg, 0.016 mmol, 62% yield) as a white solid.

TLC: $R_f$=0.24 (5% MeOH in DCM)

$^1$H NMR: (500 MHz, Methanol-$d_4$) δ 8.41 (d, J=5.2 Hz, 1H), 8.29-8.26 (m, 2H), 8.22 (s, 1H), 7.58 (d, J=3.5 Hz, 1H), 7.52 (d, J=3.5 Hz, 1H), 7.50 (d, J=2.8 Hz, 1H), 7.20 (d, J=2.9 Hz, 1H), 5.97 (ddt, J=17.2, 10.2, 7.0 Hz, 1H), 5.16-5.07 (m, 2H), 4.33 (t, J=7.1 Hz, 2H), 3.24 (s, 3H), 2.69-2.63 (m, 2H), 2.04-1.98 (m, 1H), 1.96-1.91 (m, 1H), 1.84-1.78 (m, 2H) ppm. *The three exchangeable N—H protons were not detected.

HRMS: Calc'd for $C_{26}H_{25}N_7O_2S$ [M+H$^+$]500.1863; found: 500.1860.

TABLE 1

DSF for TAFi with TAF1-2.

| Protein | Ligand | ATm + SEM (° C.) |
|---|---|---|
| TAF1-2 | DMSO | 0 ± 0.07 |
| | ZS1-589 | 1.5 ± 0.08 |
| | AZD6738 | 3.4 ± 0.1 |
| | ZS1-588 | 3.9 ± 0.05 |
| | ZS1-681.1 | 4.9 ± 0.13 |
| | ZS1-681.2 | 4.7 ± 0.13 |
| | GNE-371 | 8.5 ± 0.1 |

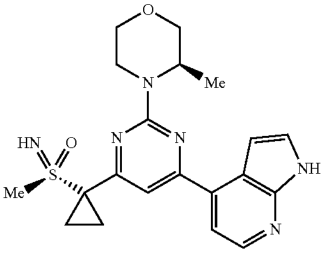

ZS1-588

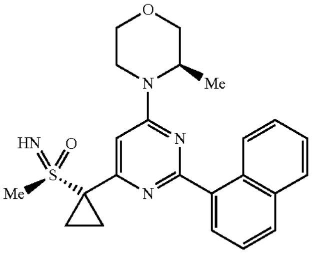

ZS1-589

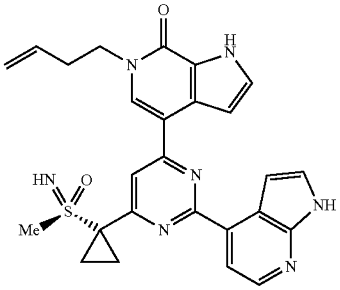

ZS1-681

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A compound of Formula II (II)

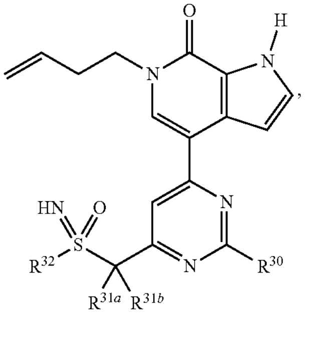, or a pharmaceutically acceptable salt thereof, wherein:

$R^{30}$ is selected from $R^{30a}$ or —NH—$R^{30a}$;

$R^{30a}$ is selected from unsubstituted or substituted aryl, unsubstituted or substituted heteroaryl, substituted or unsubstituted cycloalkyl, and unsubstituted or substituted heterocycloalkyl;

$R^{31a}$ and $R^{31b}$ are brought together with the carbon to which they are attached to form a substituted or unsubstituted cycloalkyl ring or a substituted or unsubstituted heterocycloalkyl ring;

$R^{32}$ is selected from $R^{32a}$ or —NH—$R^{32b}$;

$R^{32a}$ is selected from substituted or unsubstituted $C_1$-$C_6$ alkyl, substituted or unsubstituted aryl, substituted or unsubstituted cycloalkyl, substituted or unsubstituted heterocycloalkyl, —($C_1$-$C_6$ alkyl)-(substituted or unsubstituted aryl), —($C_1$-$C_6$ alkyl)-(substituted or unsubstituted heteroaryl), —($C_1$-$C_6$ alkyl)-(substituted or unsubstituted cycloalkyl), and —($C_1$-$C_6$ alkyl)-(substituted or unsubstituted heterocyloalkyl); and $R^{32b}$ is selected from hydrogen, substituted or unsubstituted $C_1$-$C_6$ alkyl, substituted or unsubstituted aryl, substituted or unsubstituted cycloalkyl, substituted or unsubstituted heterocycloalkyl, —($C_1$-$C_6$ alkyl)-(substituted or unsubstituted aryl), —($C_1$-$C_6$ alkyl)-(substituted or unsubstituted heteroaryl), —($C_1$-$C_6$ alkyl)-(substituted or unsubstituted cycloalkyl), and —($C_1$-$C_6$ alkyl)-(substituted or unsubstituted heterocyloalkyl).

2. The compound of claim 1, wherein $R^{30}$ is $R^{30a}$.

3. The compound of claim 1, wherein $R^{30}$ is —NH—$R^{30a}$.

4. The compound of claim 1, wherein $R^{30a}$ is unsubstituted or substituted aryl.

5. The compound of claim 1, wherein $R^{30a}$ is unsubstituted or substituted heteroaryl.

6. The compound of claim 1, wherein $R^{30a}$ unsubstituted or substituted heterocycloalkyl.

7. The compound of claim 1, wherein $R^{30}$ is selected from:

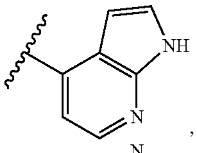, 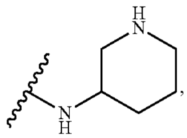,

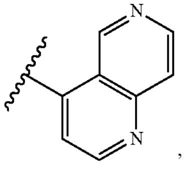, 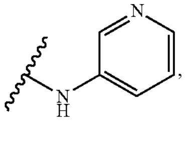, and

-continued

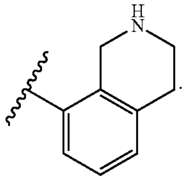

8. The compound of claim 1, wherein $R^{31a}$ and $R^{31b}$ are brought together with the carbon to which they are attached to form a substituted or unsubstituted cycloalkyl ring.

9. The compound of claim 1, wherein $R^{31a}$ and $R^{31b}$ are brought together with the carbon to which they are attached to form a substituted or unsubstituted heterocycloalkyl ring.

10. The compound of claim 1, wherein $R^{31a}$ and $R^{31b}$ are brought together with the carbon to which they are attached to form:

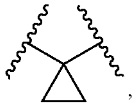
,
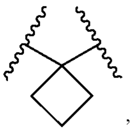
,
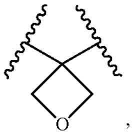
, or
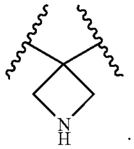
.

11. The compound of claim 1, wherein $R^{32}$ is $R^{32a}$.

12. The compound of claim 11, wherein $R^{32a}$ is $C_1$-$C_6$ alkyl or —($C_1$-$C_6$ alkyl)-(substituted or unsubstituted aryl).

13. The compound of claim 11, wherein $R^{32a}$ is methyl.

14. The compound of claim 1, wherein $R^{32}$ is —NH—$R^{32b}$.

15. The compound of claim 14, wherein $R^{32b}$ is hydrogen or —($C_1$-$C_6$ alkyl)-(substituted or unsubstituted aryl).

16. The compound of claim 1, wherein $R^{32}$ is selected from:

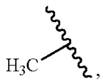
,
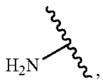
,
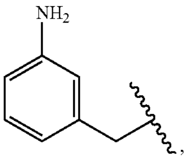
, and
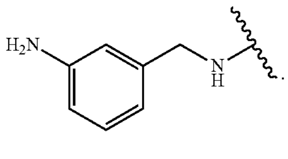
.

17. The compound of claim 1, wherein the compound is selected from:

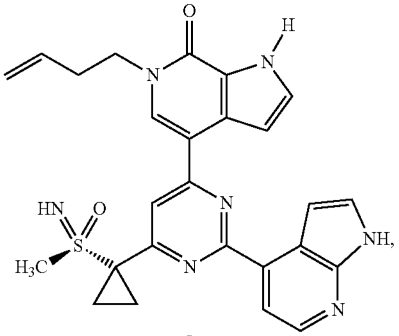

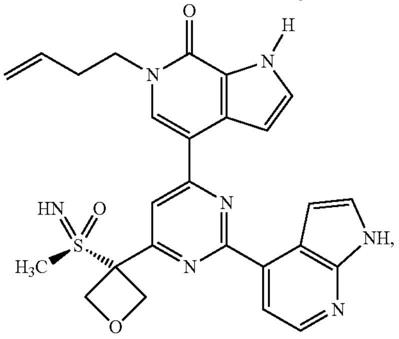

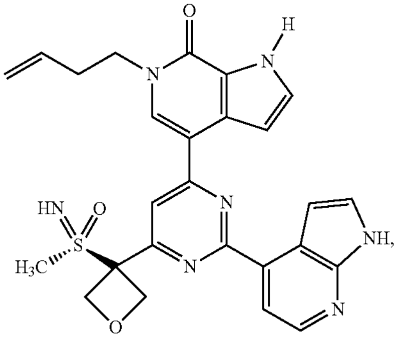

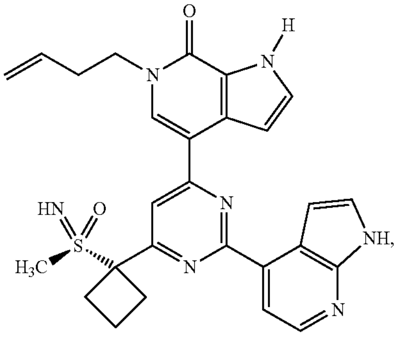

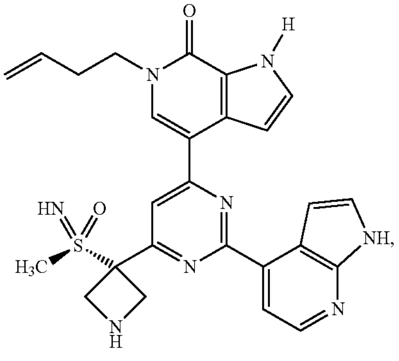

-continued

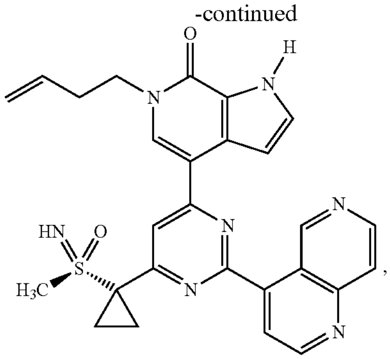

,

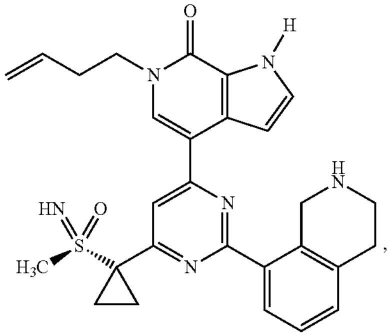

,

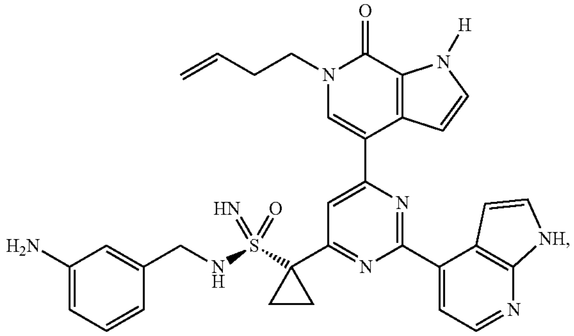

,

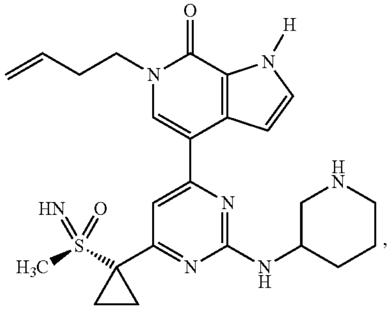

,

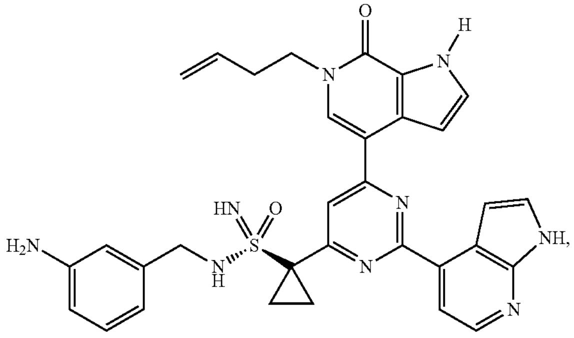

-continued

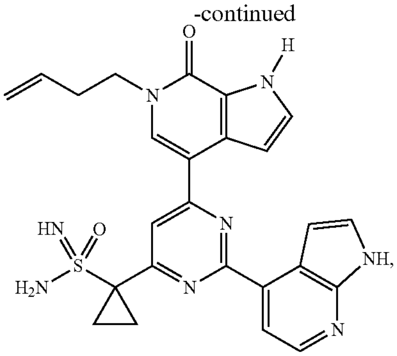

,

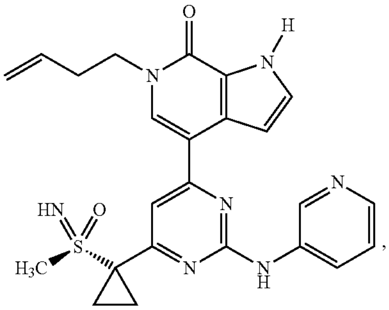

,

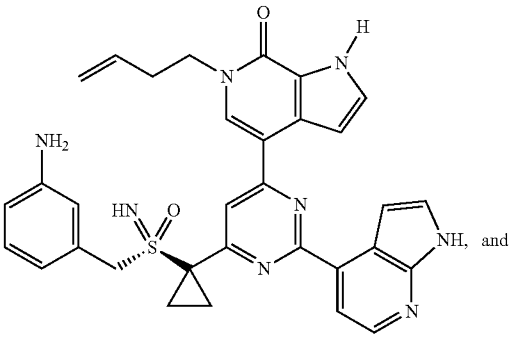

, and

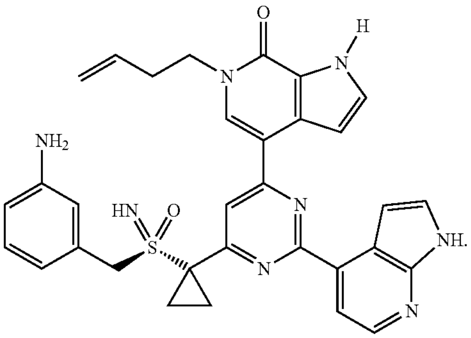

.

18. A pharmaceutical composition comprising a therapeutically effective amount of a compound of claim 1, or a pharmaceutically acceptable salt thereof, and a pharmaceutically acceptable carrier.

19. A method for the treatment of a disorder of uncontrolled cellular proliferation associated with TAF1 dysfunction in a mammal comprising the step of administering to the mammal an effective amount of a compound of claim 1, or a pharmaceutically acceptable salt thereof.

20. The method of claim 19, wherein the disorder is cancer.

* * * * *